US007989611B2

(12) United States Patent
Mashko et al.

(10) Patent No.: US 7,989,611 B2
(45) Date of Patent: Aug. 2, 2011

(54) EXPRESSION CONTROL SEQUENCE

(75) Inventors: Sergei Vladimirovich Mashko, Moscow (RU); Danila Vadimovich Zimenkov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 983 days.

(21) Appl. No.: 11/002,141

(22) Filed: Dec. 3, 2004

(65) Prior Publication Data

US 2005/0266525 A1 Dec. 1, 2005

Related U.S. Application Data

(63) Continuation of application No. 10/068,851, filed on Feb. 11, 2002, now abandoned.

(30) Foreign Application Priority Data

Feb. 22, 2001 (RU) ............................... 2001104817

(51) Int. Cl.
*C07H 21/04* (2006.01)
*C07H 21/02* (2006.01)
(52) U.S. Cl. ....................... 536/24.1; 536/23.1; 536/23.2
(58) Field of Classification Search .................. None
See application file for complete search history.

(56) References Cited

U.S. PATENT DOCUMENTS 5,850,018 A 12/1998 Baszczynski et al.
5,858,773 A 1/1999 Mazodier et al.

FOREIGN PATENT DOCUMENTS

EP 0 186 069 A2 7/1986
WO WO 92/04452 A1 3/1992
WO WO 97/05260 A2 2/1997

OTHER PUBLICATIONS

Landick and Yankofsky (*Escherchia coli* and *Salmonella typhimuriun* Cellular and Molecular Biology, 1987, F. Niedhardt Ed., Transcription Attenuation, pp. 1276-1301.*
Kahala et al. (Appl. Microbiol. Biotechnol., 1999, 51:71-78).*

C.L. Chan, et al., J. Miol. Biol., vol. 268, pp. 54-68, "Multiple Interactions Stabilize a Single Paused Transcription Intermediate in Which Hairpin to 3' End Spacing Distinguishes Pause and Termination Pathways", 1997.
R. Landick, et al., Journal of Molecular Biology, vol. 216, No. 1, pp. 25-37, XP-001069618. "Replacement of the *Escherichia coli* TRP Operon Attenuation Control Codons Alters Operon Expression", 1990.
K. Sano, et al. Gene, vol. 53, No. 2-3, pp. 191-200, XP-001069039, "Structure and Function of the TRP Operon Control Regions of *Brevibacterium lactofermentum*, A Glutamic-Acid-Producing Bacterium", 1987.
K.V. Konan, et al., Journal of Bacteriology, vol. 179, No. 5, pp. 1774-1779, XP-002200339, "Regulation of the *Escherichia coli* TNA Operon: Nascent Leader Peptide Control at the TNAC Stop Codon", Mar. 1997.
C.L. Turnbough Jr., et al., Proc. Natl. Acad. Sci., vol. 80, pp. 368-372, XP-001070869, "Attenuation Control of Pyrbi Operon Expression in *Escherichia coli* K-12", Jan. 1983.
C. Lui, et al., Journal of Bacteriology, vol. 171, No. 6, pp. 3337-3342, XP-001070867, "Multiple Control Mechanisms for Pyrimidine-Medicated Regulation of Pyrbi Operon Expression in *Escherichia coli* K-12", Jun. 1989.
Chopin, A. FEMS Microbiology Reviews, 1993; 12: 21-38.
Gish and Yanofsky. J. Bacteriol. 1995; 177(24):7245-54.
Jeng et al. Can. J. Microblol. 1997; 43:1147-1156.
Lu et al. J. Bacteriol. Jan. 2001; 183(2):490-99.
Bae, Y. M, et al., "The *Rhizobium meliloti* trpE(G) Gene Is Regulated by Attenuation, and Its Product, Anthranilate Synthase, Is Regulated by Feedback Inhibition," Journal of Bacteriology, vol. 172, No. 6, Jun. 1990, pp. 3318-3327.
Bae, Y. M., et al, "Genetic Analysis of the Attenuator of the *Rhizobium meliloti* trpE(G) Gene," Journal of Bacteriology, vol. 173, No. 11, Jun. 1991, pp. 3382-3388.

* cited by examiner

*Primary Examiner* — Michele K Joike
(74) *Attorney, Agent, or Firm* — Oblon, Spivak, McClelland, Maier & Neustadt, L.L.P.

(57) ABSTRACT

An expression control sequence which controls expression of a target gene linked downstream of the expression control sequence depending on an intracellular concentration of an amino acid, wherein in a bacterial cell which harbors a DNA construct comprising the expression control sequence, a promoter linked upstream of the expression control sequence and the target gene linked downstream of the expression control sequence, frequency of termination in the expression control sequence, of transcription starting from the promoter is lowered by increase of an intracellular concentration of an amino acid, whereby expression of the target gene increases.

21 Claims, 9 Drawing Sheets

EXPRESSION CONTROL SEQUENCE

CROSS-REFERENCE TO A RELATED APPLICATION

The present application is a continuation of U.S. Ser. No. 10/068,851, filed on Feb. 11, 2002, which claims priority to Russian Patent Application No. RU 2001104817, filed on Feb. 22, 2001.

BACKGROUND OF THE INVENTION

The present invention relates to the microbiological industry. In particular, the present invention relates to the development of a new approach to regulated gene expression in bacterial cells.

Induction of expression of genes cloned into recombinant bacteria (e.g., *E. coli*) by the addition of the relatively simple and cheap chemical compounds is a very attractive idea for many biotechnological processes. Among the group of potential attractive inducer candidates are natural L-amino acids.

To the knowledge of the present inventors, the regulatory regions of the tryptophanase genes represent unique natural systems induced by addition of tryptophan to a cultural medium [Landick R., Turnbough C. L., Yanofsky C. "Transcription attenuation"/ In: "*Escherichia coli* and *Salmonella*. Cellular and molecular biology" (Second Edition, F. C. Neidhardt—Editor in Chief), (1996), pp. 1263-1286]. In contrast, there are the several known systems in which the controlled gene expression is decreased in the presence of an excess of amino acids in the cells (for example, the system of the trp-operon repressor-operator [Platt, T. "Regulation of gene expression in the tryptophan operon of *Escherichia coli*"/In: "The Operon" (Miller, J. H., Reznikoff, W. S.—Eds.), Cold Spring Harbor Laboratory (1978), pp. 263-302.], and the attenuation of amino acid operon transcription [Landick R., Turnbough C. L., Yanofsky C. "Transcription attenuation"/ In: "*Escherichia coli* and *Salmonella*. Cellular and molecular biology" (Second Edition, F. C. Neidhardt—Editor in Chief), (1996), pp. 1263-1286]).

The molecular mechanism of transcription attenuation in amino acid operons is based on the possibility of alternative mRNA secondary structure formation in the "attenuator" region as a result of translation of the "leader" peptide located upstream from the first structural gene of the operon. The coding region of the leader peptide gene is enriched by the codons of the sense amino acid (i.e., the codon of those amino acid whose biosynthesis is provided by the corresponding gene product encoded by the operon). For example, for the trp-operon, the leader peptide gene is enriched with Trp-codons, for the his-operon—His-codons, for the thr-operon—Thr-codons and Ile-codons, etc).

The details of this well-established regulation of transcription are presented in the FIG. 1, using the attenuator regions of the *E. coli* trp- and his-operons as examples. As shown in FIG. 1, alternative mRNA secondary structures can be formed during transcription of the corresponding DNA fragments: the hairpins t1:t2 and t3:t4, or their alternative—t2:t3, can be formed for trp-leader, analogously, h1:h2, h3:h4 and h5:h6, or h2:h3 and h4:h5 can be formed for his-leader. The hairpins t3:t4 and h5:h6 are the typical ρ-independent transcription terminators. Accordingly, their formation during the elongation of transcription leads to termination in the attenuator regions of the corresponding operon preventing the expression of the structural genes of the operon.

The process of mRNA secondary structure formation is coupled to the process of mRNA synthesis. Therefore, the hairpins t1:t2 and then t3:t4 are formed step by step (its alternative—the hairpin t2:t3 could not be formed because t1:t2 has already been formed) in the trp-attenuator when the leader peptide has not been translated. Analogously, rapid formation of, in succession, the hairpins h1:h2, h3:h4, and h5:h6 prevents the formation of their alternative structures—h2:h3 and h4:h5 during synthesis of his-attenuator mRNA without translation of the corresponding leader peptide.

As discussed above, the formation of the hairpins t3:t4, as well as h5:h6 leads to termination in the corresponding attenuator regions. This situation could be realized during in vitro transcription of the corresponding DNAs by a pure RNA polymerase without any translational factors in the reaction mixture, or in vivo under general amino acid starvation conditions.

A much more complicate situation may occur in vivo during translation of the leader peptide when excessive sense amino acid is present (more precisely, the corresponding charged tRNA is in excess), or a deficiency of the same occurs in the bacterial cell. It has been shown that RNA polymerase initiating attenuator mRNA transcription stops at the pause site in the region located immediately downstream from the hairpin 1:2 (probably, the formation of this hairpin is the essential, but not the adequate condition of such pausing) [Chan, C. L., Wang, D., Landick, R. "Multiple interactions stabilize a single paused transcription intermediate in which hairpin to 3' end spacing distinguishes pause and termination pathway"/ J. Mol. Biol. 268 (1997) 54-68]. The ribosome translating the N-terminal part of the leader peptide releases the RNA polymerase followed by continuation of transcriptional elongation and, thus, enabling the formation of the alternative mRNA hairpin (2:3). The following events depend on the intracellular concentration of the charged-tRNA(s) of the sense amino acid, because the corresponding codons of the leader peptide gene have to be translated by the ribosome following charging of the respective tRNA.

Under sense amino acid starvation conditions, the ribosome stalls at the sense codon and the hairpin 2:3 is left uninterrupted. In the scenario, while RNA polymerase synthesizes the downstream fragment of the mRNA which, in principle, could form the terminator hairpin (t3:t4—for the trp-attenuator and h5:h6—for the his-attenuator), but it does not fold due to the existence of the alternative hairpin (t2:t3—for the trp, and the structure h2:h3, h4:h5—for the his), followed by transcription elongation and synthesis of the mRNA of the operon structural genes.

In the presence of an excess of the sense amino acid, the translation of the leader peptide occurs with high efficiency. In this scenario, the ribosome initially disrupting the hairpin 1:2, disrupts the hairpin 2:3, as well, and stalls at the stop codon of the leader peptide. The stall at the stop codon of the leader peptide leads to formation of the terminator hairpin and to the termination of transcription in the attenuator region.

SUMMARY OF THE INVENTION

An object of the present invention is the creation of a new artificial prokaryotic regulatory system, which provides increased controlled gene expression triggered by an increase in intracellular concentration of the "sense" amino acid.

The present inventors have succeeded in creating a new artificial regulatory system in which expression depends on the intracellular amino acid concentration by the exploiting the native regulatory mechanism of said amino acid based on the formation of the alternative mRNA secondary structures based on the efficiency of the leader peptide translation. In contrast to the natural attenuators of amino acid operons, the new system provides an increase in controlled gene expression in the presence of an excess of the intracellular sense amino acid concentration. In addition, the level of expression of genes under the control of the new expression control sequence is decreased under sense amino acid starvation conditions. Unlike the well-known transcription regulation of its progenitor (attenuation of amino acid operon transcription), the system of the present invention results in an increase in controlled gene expression in the presence of an excess of the sense amino acid.

The present invention provides an expression control sequence, as well as an expression control method and a production method using the expression control sequence, as mentioned below:

(1) An expression control sequence which controls expression of a target gene linked downstream of the expression control sequence, wherein said control depends on the intracellular concentration of an amino acid, wherein in a bacterium, which harbors a DNA construct comprising the expression control sequence, a promoter sequence is linked upstream of the expression control sequence and a target gene is linked downstream of the expression control sequence, frequency of termination in the expression control sequence when transcription initiates from the promoter is decreased due to an increased intracellular concentration of an amino acid, whereby expression of the target gene increases.

(2) The expression control sequence according to (1), which comprises a region coding for a leader peptide comprising said amino acid and a ρ-independent terminator, wherein when translation of the leader peptide stops at the codon of said amino acid in the course of the translation under starvation conditions of the amino acid, a base paring structure of the ρ-independent terminator is formed in a transcript of the expression control sequence, whereby the frequency of termination in the expression control sequence, of the transcription increases.

(3) The expression control sequence according to (2), which comprises an odd number of not less than 3 segments, wherein each of the segments can form a base pairing structure together with its adjacent segment, and wherein in the transcript of the expression control sequence, when a segment or segments other than terminal segments each form a base pairing structure with one of its two adjacent segments, the segment or segments each do not form a base pairing structure with the other of the two adjacent segments; a first segment at an upstream terminal overlaps with the region interacting with the ribosome translating the leader peptide; a second segment adjacent to the first segment forms a base pairing structure with a third segment adjacent to the second segment in the course of the translation of the leader peptide; and a base paring structure formed from the downstream terminal segment and its adjacent segment is the base paring structure of the ρ-independent terminator.

(4) The expression control sequence according to (3), wherein the first segment overlaps with the codon of the amino acid in the leader peptide.

(5) The expression control sequence according to (3) or (4), wherein the number of the segments is 5.

(6) The expression control sequence according to any of (3) to (5), wherein the sequence of each segment, or a part thereof, and the sequence of the adjacent segment, or a part thereof, constitute an inverted repeat sequence.

(7) The expression control sequence according to any of (2) to (6), wherein the ρ-independent terminator is capable of functioning in a bacterium belonging to the genus *Escherichia*, the genus *Salmonella*, or the genus *Serratia*.

(8) The expression control sequence according to (7), wherein the ρ-independent terminator is capable of functioning in a bacterium belonging to the genus *Escherichia*.

(9) The expression control sequence according to (7) or (8), which comprises five segments an1 to an5 in order from an upstream side, wherein the segments an1 and an2, and a coding region for the leader peptide are derived from a sequence of an attenuator of a tryptophan operon of *Escherichia coli*, the segments an4 and an5 are derived from a sequence of an attenuator of a histidine operon of *Escherichia coli*, and the segment an3 is derived from a combination of the sequences of the attenuators of the tryptophan operon and the histidine operon.

(10) The expression control sequence according to (9), wherein the leader peptide has been modified to contain not less than 2 tryptophan residues.

(11) A method for controlling an expression of a target gene, comprising the steps of:

cultivating a bacterium harboring a DNA construct comprising the expression control sequence as defined in any of (1) to (10), a promoter linked upstream of the expression control sequence and the target gene linked downstream of the expression control sequence in a culture medium, and changing an intracellular concentration of an amino acid on which expression control by the expression control sequence depend, to control expression of the target gene.

(12) A method for producing a target substance comprising the steps of cultivating a bacterium capable of producing the substance to produce the substance and collecting the substance, wherein the bacterium harbors a DNA construct comprising the expression control sequence as defined in any of (1) to (10), a promoter linked upstream of the expression sequence and a target gene which has relationship to production of the target substance and is linked downstream of the expression control sequence, and an intracellular concentration of an amino acid on which expression control by the expression control sequence depend, is changed to control expression of the target gene.

(13) The method according to (12), wherein the intracellular concentration of the amino acid is changed by synthesis or degradation of the amino acid by the bacterium.

Accordingly, the present invention provides an expression control sequence in which controlled gene expression is increased as a result of increasing intracellular concentration of the sense amino acid. According to the expression control method of the present invention, expression of the target gene can be increased by increasing the intracellular concentration of the sense amino acid. According to the production method of the present invention, the production amount of the target substance can be increased by increasing the intracellular concentration of the sense amino acid, thus the target substance can be efficiently produced.

BRIEF EXPLANATION OF THE DRAWINGS

FIG. 2 shows detailed structures of the native attenuators and the artificial anti-attenuator. Notably FIG. 2 is a fragmented view, where FIG. 2A shows the left half of the full figure, while In FIG. 2, A and B represent the proposed "downstream" boarder of the parts of mRNA which are protected by the ribosome stalling at "sense" codons (A) and terminating at the stop codon (B) of the "leader" peptide, respectively. C represents the pause site of DNA transcription by E. coli RNA polymerase. The native Trp attenuator corresponds to SEQ ID NO: 19, the native His attenuator corresponds to SEQ ID NO: 20, and the artificial TrpHis anti-attenuator corresponds to SEQ ID NO: 21.

FIG. 3 shows the general scheme of construction of the artificial anti-attenuator. The cross-in-circle mark represents nucleotide mutations in comparison to the native sequence. BI: BamHI, Bg: BglII, NI: NdeI, XI; XbaI, XI*; XbaI(dam⁻). Notably FIG. 3 is a fragmented view, where FIGS. 3B and 3C represent a flow chart diagramming the specific details of the general scheme.

DETAILED DESCRIPTION OF THE INVENTION

<1> Expression Control Sequence

Figure 1:
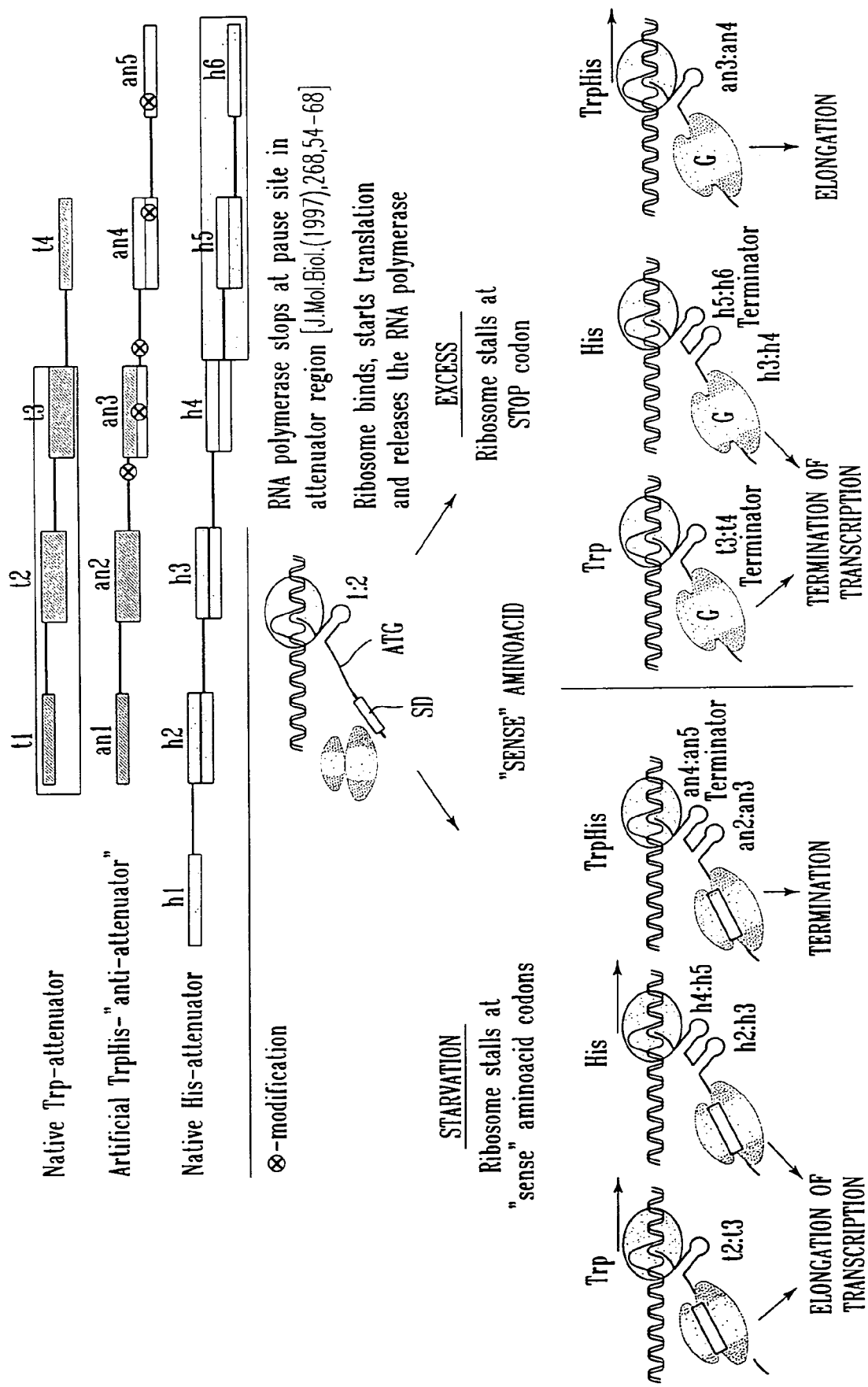
FIG. 1 shows the explanatory scheme of the structures and properties of the native attenuators and the expression control sequence (artificial anti-attenuator) of the present invention.

The expression control sequence of the present invention is an expression control sequence which controls expression of a target gene linked downstream of the expression control sequence, wherein expression depends on the intracellular concentration of an amino acid (i.e., sense amino acid), wherein in a bacterium, which harbors a DNA construct comprising the expression control sequence, a promoter sequence is linked upstream of the expression control sequence and a target gene is linked downstream of the expression control sequence, frequency of termination in the expression control sequence when transcription initiates from the promoter is lowered by increase of an intracellular concentration of an amino acid, whereby expression of the target gene increases.

The identity of the sense amino acid is not restricted provided that its aminoacyl tRNA can be synthesized and the synthesized aminoacyl tRNA can be used for translation of a protein in a bacterium for which the expression control sequence of the present invention is used. Preferably, the sense amino acid is tryptophan, histidine, phenylalanine, threonine, leucine, isoleucine, or valine.

Examples of the target gene include chloramphenicolacetyltransferase gene (cat), amino acid operons, genes of which protein products are involved in the biosynthesis of amino acids, nucleosides and nucleotides, and genes encoding the foreign protein products.

Examples of the promoter include $P_{tac}$, and any other regulated and constitutive prokaryotic promoters.

Examples of the bacterium which harbors the DNA construct include bacteria belonging to the genuses Escherichia, Salmonella, and Serratia.

The construction of the expression control sequence and the DNA construct and preparation of the bacterium harboring the DNA construct can be performed according to standard genetic engineering techniques (for example, see Molecular Cloning, 2$^{nd}$ Edition, Cold Spring Harbor Press (1989), Japanese Patent Application Laid-Open No. 2-207791 and the like). Also by standard techniques, it is also possible to determine decreases of frequency of termination in the expression control sequence, of transcription starting from the promoter by increase of an intracellular concentration of an amino acid, whereby expression of the target gene increases.

In regard to the intracellular concentration of the sense amino acid, if a relationship between the intracellular and extracellular concentrations in the bacterium is known, it is not necessary to directly measure the intracellular concentration. In this scenario, intracellular concentration may be estimated based on the extracellular concentration, such as a concentration in a medium. The frequency of termination in the expression control sequence (i.e., transcription starting from the promoter) is not necessary to be directly measured either and it is sufficient to determine increase of the target gene expression. The increase of the target gene expression can be determined by measuring an amount of the gene product of the target gene, or an activity of the gene product when the gene product has an activity.

An embodiment for the lowering of frequency of termination in the expression control sequence (transcription starting from the promoter by increase of an intracellular concentration of an amino acid), whereby expression of the target gene increases, is exemplified by an embodiment in which the transcription starting from the promoter is terminated in the expression control sequence when the intracellular concentration of the sense amino acid is not higher than a certain level, and the transcription is elongated when the intracellular concentration of the sense amino acid is higher than the certain level, thereby expressing the target gene.

The expression control sequence of the present invention preferably comprises a region coding for a leader peptide comprising the sense amino acid and a ρ-independent terminator. In this embodiment, when translation of the leader peptide stops at codon of the sense amino acid (sense codon) in the course of translation under sense amino acid starvation conditions, a base pairing structure of the ρ-independent terminator is formed in a transcript of the expression control sequence, whereby the frequency of termination in the expression control sequence (and thus transcription) increases.

The length of the leader peptide is usually 14 to 32 residues. The leader peptide usually contains 14 to 57%, preferably 30 to 45% of sense amino acid residues based on the total amino acid residues. As the proportion of the sense amino acid becomes large, control by the intracellular concentration of the sense amino acid becomes correspondingly more strict.

The ρ-independent terminator has a sequence that can form a base pairing structure (hairpin) and terminates transcription when the base pairing structure is formed. The ρ-independent terminator is preferably one that is capable of functioning in a bacterium belonging to the genus *Escherichia, Salmonella,* or *Serratia*.

The means of allowing the base pairing structure of the ρ-independent terminator to be formed in the transcript of the expression control sequence when translation of the leader peptide stops at the sense codons in the course of the translation, is exemplified by providing an expression control sequence having an odd number of not less than 3 segments, wherein each of the segments can form a base pairing structure together with its adjacent segment, and wherein in the transcript of the expression control sequence, when a segment or segments other than terminal segments each form a base pairing structure with one of its two adjacent segments, the segment or segments each do not form a base pairing structure with the other of the two adjacent segments. In this embodiment, a first segment at an upstream terminal overlaps with the region interacting with the ribosome translating the leader peptide, a second segment adjacent to the first segment forms a base pairing structure with a third segment adjacent to the second segment in the course of the translation of the leader peptide, and a base pairing structure formed from the downstream terminal segment and its adjacent segment is the base pairing structure of the ρ-independent terminator.

In this embodiment, it is necessary that the formation of the base pairing structure between the first segment and the second segment is blocked by stopping of the ribosome at the codon of the sense amino acid. Because of the mass of the ribosome, the ribosome covers a region of from about 17 bp upstream from the codon of the sense amino acid where the ribosome stops, to about 13 bp downstream from the codon of the sense amino acid. The region interacting with the ribosome means such a region that is covered by the ribosome. If the first segment overlaps with the region interacting with the ribosome translating the leader peptide, it is predicted that the formation of the base pairing structure between the first segment and the second segment is sufficiently blocked by stopping of the ribosome at the codon of the sense amino acid. For example, if the codon of the sense amino acid exists immediately before the termination codon of the leader peptide and the distance from the codon of the sense amino acid to the starting point of the first segment is within about 13 bp, the formation of the base pairing structure between the first segment and the second segment can be blocked.

The first segment overlaps with the codon of the sense amino acid in the leader peptide.

In this embodiment, when the first segment is blocked by a ribosome due to sense amino acid starvation, the base pairing structures between the second and the third, the forth and the fifth, . . . are formed and the final base pairing structure functions as a terminator to terminate the transcription. On the other hand, when the sense amino acid is sufficiently provided and ribosome moves along mRNA to a stop codon at a sufficient rate to follow the progress of the transcription, resulting in block of up to the second segment by ribosome, the base pairing structures between the third and the forth, . . . are formed to prevent formation of a terminator.

In the expression control sequence of the present invention, it is preferred that a pause site for RNA polymerase exists in the region encoding the C-terminal region of the leader peptide, or downstream from the region encoding the leader peptide, more preferably in a region from the second segment to the third segment. When no pause site exists, the expression of the target gene may not be sufficiently controlled if translation associated with transcription does not sufficiently occur.

The number of the segments is, for example, 5.

The nucleotide sequence of each segment may be one that can form a base pairing structure with its adjacent segment. For example, the sequence of each segment or a part thereof and the sequence of the adjacent segment or a part thereof may constitute an inverted repeat sequence. The sequence constituting the inverted repeat may not be continuous. In other words, it may contain a part making no base pair within its sequence. In the segment other than the terminal segments, it is sufficient that there is at least a partial overlap between a part constituting the inverted repeat sequence with one of its adjacent segments and a part constituting the inverted repeat sequence with other of its adjacent segments.

An example of the expression control sequence is one which comprises five segments an1 to an5 in order from an upstream side, wherein the segments an1 and an2, and a coding region coding for the leader peptide are derived from a sequence of an attenuator of a tryptophan operon of *Escherichia coli*, the segments an4 and an5 are derived from a sequence of an attenuator of a histidine operon of *Escherichia coli*, and the segment an3 is derived from a combination of the sequences of the attenuators of the tryptophan operon and the histidine operon.

The term "derived from" used herein means to have a sequence which is the same as or similar to the native sequence. The means of obtaining the sequence is not restricted. The sequence may be isolated from a biological material or chemically synthesized. The similar sequence may be a sequence which has substitution, deletion or insertion of one or more nucleotides in the native sequence and which can form a base pairing structure equivalent to that formed in the native sequence.

In the preferred example of the expression control sequence, the leader peptide is preferably one that has been modified to contain not less than 2 tryptophan residues. These tryptophan residues are preferably continuous.

The present invention is described with reference to the preferred example of the expression control sequence. The expression control sequence is hereinafter referred to as an artificial anti-attenuator for convenience' sake.

The biological properties of the artificial anti-attenuator are schematically presented in FIG. 1. As could be seen from FIG. 1, under sense amino acid starvation conditions and the stalling of the ribosome at the corresponding codons of the leader peptide, the undisrupted hairpin an2:an3 of the anti-attenuator would form a hairpin an4:an5 that is the part of the typical ρ-independent transcription terminator. On the other hand, the efficient translation of the leader peptide in of the presence of an excess of the sense amino acid would lead to the disruption of the hairpin an2:an3 of the artificial anti-attenuator followed by the formation of the alternative hairpin an3:an4 that prevents the termination prior to transcription of the distal (downstream) genes, because the terminator hairpin an4:an5 could not be formed.

The construction of the artificial anti-attenuator has been designed on the basis of two well-known native attenuators of the E. coli trp- and his-operons. The native leader peptide gene of the trp-operon (trpL) having two controlling Trp-codons in its structural region was used as the leader peptide of the artificial anti-attenuator. On the other hand, the process of the alternative mRNA secondary structure formation will take place in the 3'-untranslated region of the artificial anti-attenuator like in the corresponding region of the native his-attenuator.

Figure 2A:
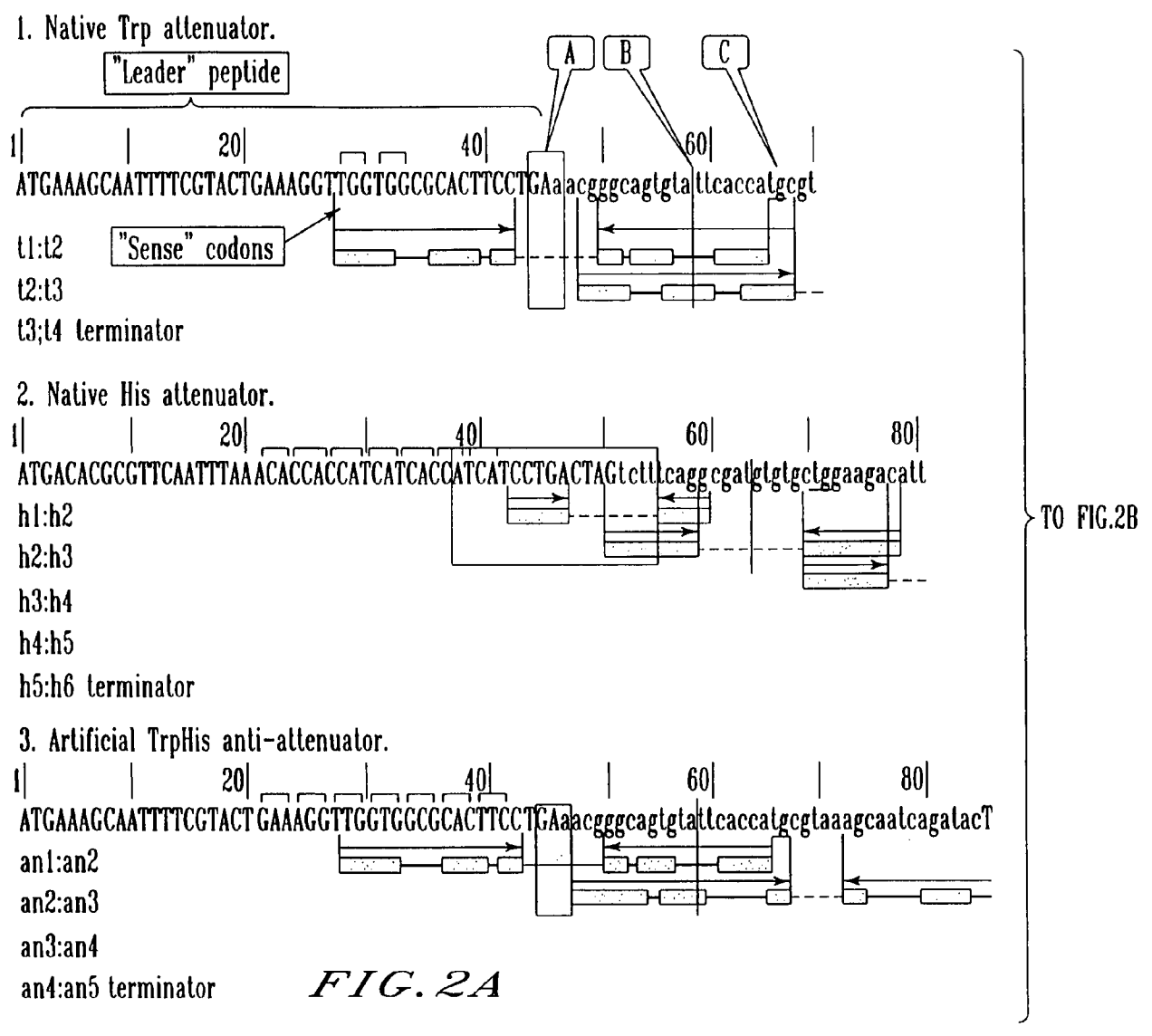
Figure 2B:
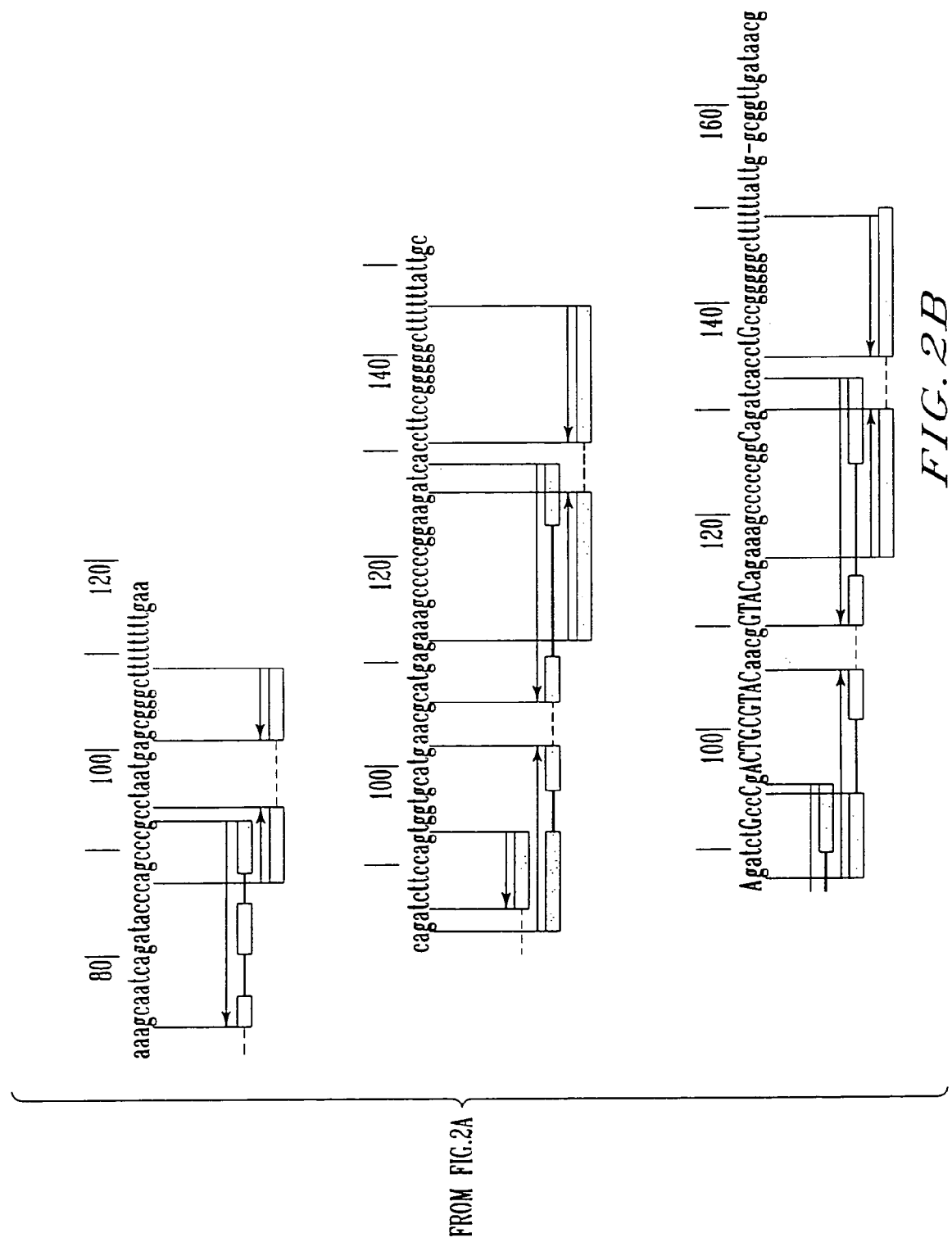
FIG. 2B shows the right half of the full figure.

The nucleotide sequences of the coding regions and the 3'-untranslated regions of two natural attenuators (trp and his) that were used as the structural foundation, as well as the sequence of the corresponding region of the artificial anti-attenuator are presented in the FIG. 2. As shown in FIG. 2, the structures up to "+85" (numbered by taking A of the ATG of the coding part of the leader peptide as "+1") from the native trp-attenuator and from the artificial anti-attenuator coincide. So, it is expected that the processes of transcription elongation with pausing RNA polymerase in the position "+66 -+67", disruption of the hairpin an1:an 2 by the ribosome translating of the leader peptide in case of Trp-starvation, as well as disruption in addition the hairpin an 2:an 3 in case of excess of Trp in the cell, would occur in the regulatory region of the artificial anti-attenuator in the same manner as the native trp-attenuator. On the other hand, the distal part of the anti-attenuator significantly differs from the corresponding regions of the his-attenuator, which has been used as the second progenitor.

Only minimal alterations were made in the region which could form the terminator hairpin an4:an5. Nevertheless, as in the native his-attenuator, the possible formation of the alternative hairpin an3:an4 is provided in the artificial anti-attenuator (the secondary structure of this region is homologous to h4:h5 of the native his-attenuator) whose formation could prevent the termination of transcription in the artificial anti-attenuator. In comparison with the native his-attenuator, in the anti-attenuator there is no DNA fragment providing formation of the h3:h4 hairpin followed by the changing of the biological properties thereof: formation of the ρ-independent transcription terminator takes place in case of the sense amino acid starvation instead of its increased intracellular concentration.

The confirmatory results of the properties of the artificial anti-attenuator are described below.

Figure 3A:
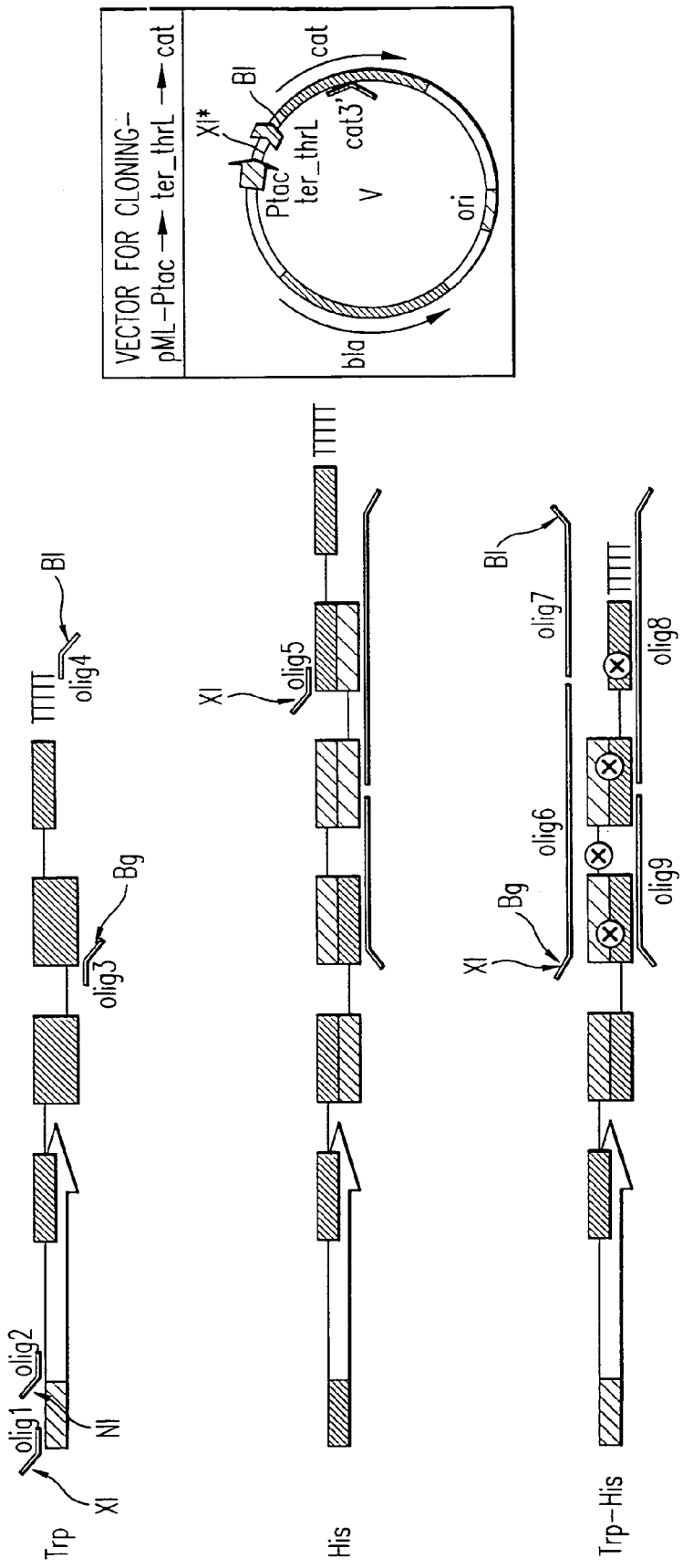
FIG. 3A shows the top portion of the figure representing the general scheme of the new artificial "anti-attenuator" regulatory element construction, FIG. 3B left half of the bottom half of the full figure.
Figure 3B:
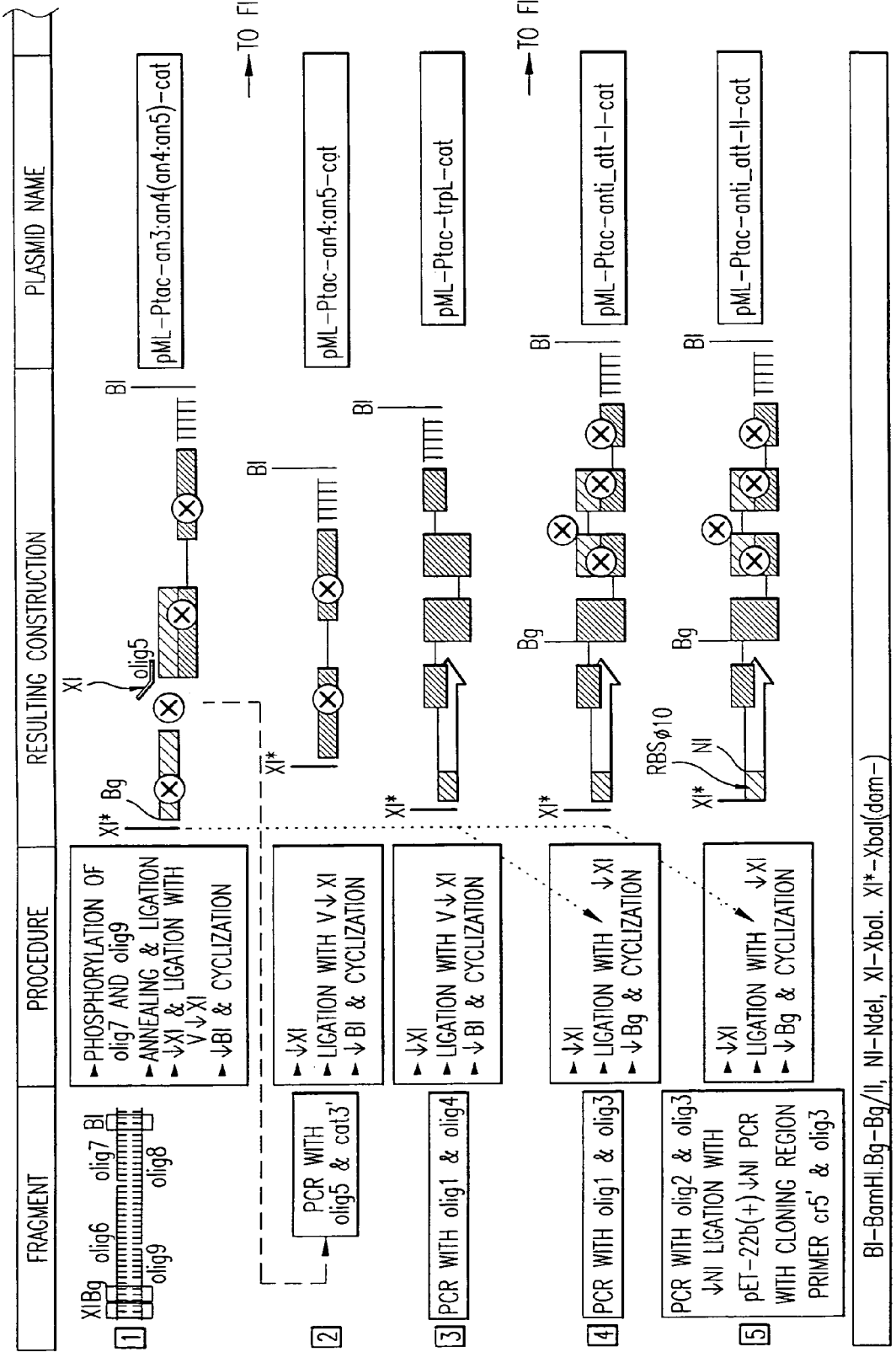
Figure 3C:
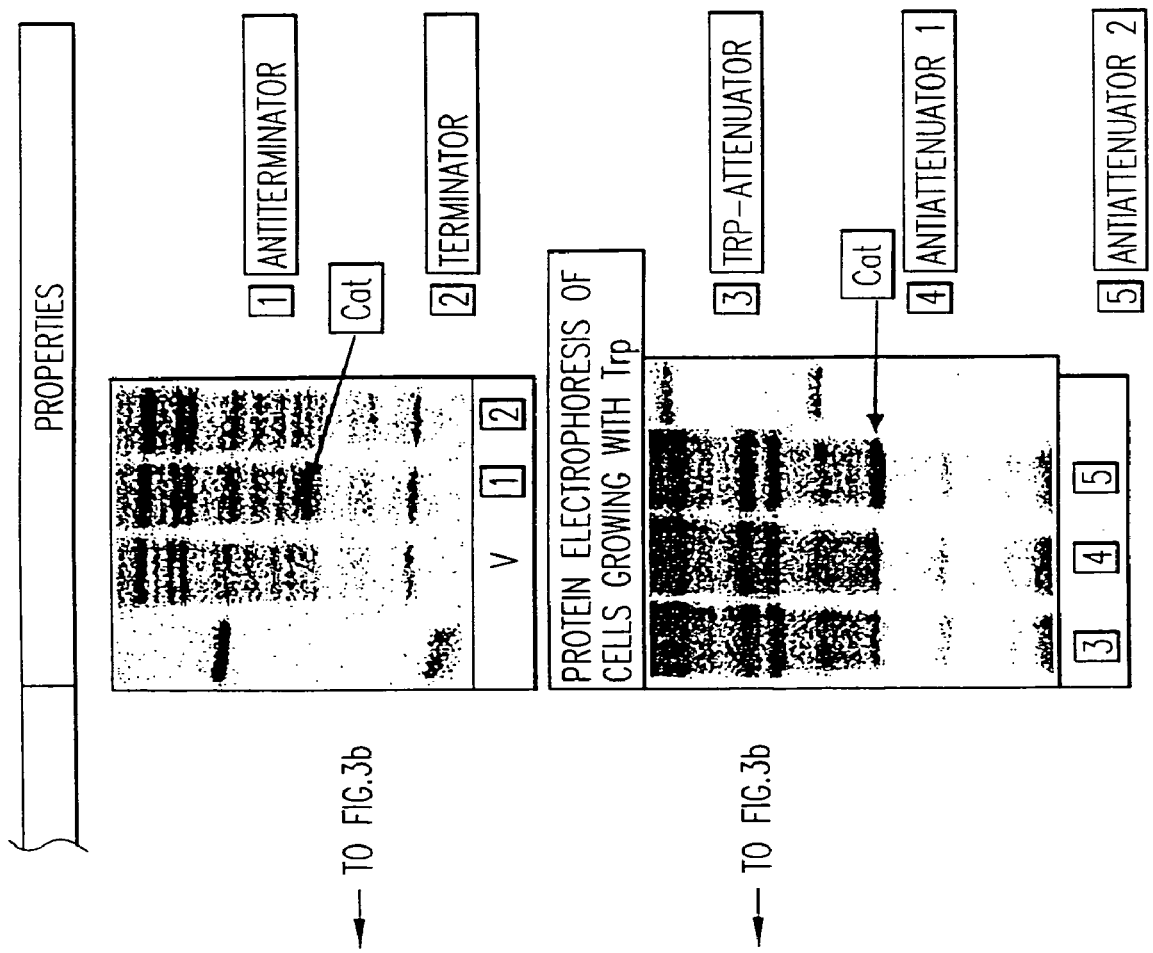
FIG. 3C shows the right half of the bottom half of the full figure.

The artificial anti-attenuator has been synthesized using standard genetic engineering techniques (including the PCR-driven amplification of the native fragment of the trp-attenuator, chemical synthesis of the oligonucleotides etc.) as schematically presented in the FIG. 3. Two different types of the artificial anti-attenuators were obtained. The native ribosome binding site (RBS) of trpL was used to provide the translation initiation of the leader peptide in the artificial anti-attenuator of the first type—anti-attenuator-I. More efficient RBS of phage T7 gene10 has been inserted in the 5'-region of the leader peptide gene in the second—anti-attenuator-II. Both artificial anti-attenuators were cloned in the vector plasmid downstream of the high-efficient promoter $P_{tac}$ and upstream of the structural part of cat gene with its own RBS. The cat gene encoding the chloramphenicolacetyltransferase (CAT), was used as a reporter and its level of expression could be used to obtain information concerning of the function efficiency of the created regulatory elements in dependence on the intracellular concentration of the sense amino acid—Trp.

Moreover, the several control recombinant plasmids were constructed on the basis of the same vector. The first plasmid carries the native attenuator of the trp-operon—trpL. The second—the potential transcription terminator—the 3'-terminal DNA fragment of the anti-attenuators providing the formation of the terminator hairpin an4:an5. The third plasmid carries the longer 3'-terminal DNA fragment of the anti-attenuators that could not provide the formation of the terminator hairpin an4:an5, because the potential alternative hairpin an3:an4 has to be formed first during the mRNA synthesis.

It is known from the literature, that the native trpL of the E. coli trp-operon (unlike the attenuators of other amino acid operons) is a rather weak attenuator: "The presence or absence of Trp in the growth medium does not normally affect readthrough of the trp attenuator; the 10-fold change in readthrough occurs only upon extreme Trp starvation in mutant bacteria or transiently upon transfer of bacteria from a Trp-containing to a Tip-free medium" [Landick R., Turnbough C. L., Yanofsky C. "Transcription attenuation"/ In: "*Escherichia coli* and *Salmonella*. Cellular and molecular biology" (Second Edition, F. C. Neidhardt—Editor in Chief), (1996), p. 1263-1286]. The later may be due to the presence of only tandem codons of the sense amino acid in the structural region of the corresponding leader peptide. Since the coding regions of the leader peptides of the artificial anti-attenuators and the native trpL are identical, the special model system has to be used for testing the regulatory properties of the new systems. The determination of the enzymatic activity of the reporter CAT was provided in the trp⁻ cells carrying the recombinant plasmids of interest, and growing under Trp-starvation conditions followed by addition of Trp in the cultural medium, if necessary. The results are presented in the Table 1.

TABLE 1

Determination of CAT activity in the strains carrying the recombinant plasmids with the tested regulatory elements.

| | | CAT activity in conditions of Trp: | |
|---|---|---|---|
| Plasmid name | Proposed properties | Starvation | Excess |
| PML-$P_{tac}$-an4:an5-cat | "terminator" | 3 ± 1 | 3 ± 1 |
| PML-$P_{tac}$-an3: an4(an4:an5)-cat | "antiterminator" | 60 ± 6 | 58 ± 6 |
| PML-$P_{tac}$-trpL-cat | Native trpL | 17 ± 3 | 9 ± 3 |
| PML-$P_{tac}$-anti_att-I-cat | "anti-attenuator-I" | 22 ± 3 | 30 ± 3 |
| pML-$P_{tac}$-anti_att-II-cat | "anti-attenuator-II" | 18 ± 3 | 51 ± 5 |

As is evident from Table 1, the level of CAT activity does not depend on the addition of the Trp to the cells carrying the plasmids without the coding part of the trpL. Moreover, the theoretical difference in the achieved level of CAT activities depending on the process of the alternative mRNA secondary structure formation could be evaluated on the basis of the results obtained for the control plasmids encoding the "terminator" and "antiterminator" hairpins. The 20-fold transcription increase could be achieved with formation of the "antiterminator" structure in comparison with the ρ-independent transcription termination in the 3'-part of the artificial anti-attenuators.

As could be suspected, the determined level of CAT activity was higher when the plasmid with the native trp-attenuator is exploited: the increased level was achieved in case of Trp-derived starvation, than after addition of Trp to the growing plasmid-carrier bacteria. The achieved level of CAT activity (17 units) could not be compared with the maximum level (60 units). That is because, at first, the Trp-derived starvation in case of bacterial growing, does not guarantee the maximal efficiency of the trpL readthrough transcription. Second, the 5'-untranslated region of cat gene located immediately upstream its own RBS, in case of exploiting of the native trpL and other tested constructions are different, so the efficiency of CAT translation initiation could differ, as well.

The primary result was obtained for the plasmids carrying the artificial anti-attenuators. As evidenced by Table 1, the increased level of CAT activity after addition of Trp to the growing bacteria was seen for the both plasmid-carrier bacterial strains. Moreover, exploiting the high-efficient RBS of phage T7 gene10 for translation initiation of the leader peptide leads to achievement of the level of CAT accumulation which is close to the theoretical maximum (51 units in comparison with 60 units). This result could be explained by the fact, that it is necessary to improve the RBS of the leader peptide to achieve the full transcription-translation coupling essential for realization of molecular mechanism of alternative mRNA secondary structure formation (typical for the native attenuation transcription in prokaryotic amino acid operons) when transcribing the artificial anti-attenuator from the rather strong promoter $P_{tac}$ (which is stronger than the native promoter of trp-operon).

The following conclusions could be made on the basis of the obtained results:
1. The process of alternative mRNA secondary structure formation may exploited for regulation of transcription: the differences in the expression level of up to 20-fold can be achieved by exploiting artificial "his-like" tails.
2. The obtained artificial "anti-attenuator" systems were functionally active:
   2.1. The presence of the coding region of the native trp-leader peptide can stimulate the process of mRNA secondary structure folding depending on the intracellular Trp-concentration.
   2.2. The best "activator"-effect in excess of Trp was found when the $P_{tac}$-promoter was exploited for transcription in combination with the optimized translation initiation of the leader peptide (exploiting of the phage T7 S10 RBS instead the native RBS of trpL).
3. It is expected that the developed system could be used as a basis of creation of the inducible regulatory elements: it could be induced by addition of the excess of Trp in the cultural medium after increasing of the quantity of the sense (Trp) amino acid codons in the structural part of the leader peptide of anti-attenuator region.

<2> Method for Controlling Target Gene Expression

The expression control method of the present invention is a method for controlling an expression of a target gene, comprising the steps of:
   cultivating a bacterium harboring a DNA construct comprising the expression control sequence of the present invention, a promoter linked upstream of the expression control sequence and the target gene linked downstream of the expression control sequence in a culture medium, and
   changing an intracellular concentration of an amino acid (sense amino acid) on which expression control by the expression control sequence depend, to control expression of the target gene.

The DNA construct and the bacterium harboring the DNA construct may be as described above with respect to the expression control sequence.

The culture conditions are not restricted provided that the bacterium can survive. The conditions are properly selected depending on the bacterium.

The method of changing an intracellular concentration of the sense amino acid is exemplified by a method of changing a concentration of the sense amino acid in the medium in which the bacterium is cultured, a method of changing an amount of synthesis or degradation of the sense amino acid in cells. The change of the target gene expression can be determined by measuring an amount of the gene product of the target gene, or by measuring an activity of the gene product when the gene product has an activity.

<3> Method for Producing Target Substance

The production method of the present invention is a method for producing a target substance comprising the steps of cultivating a bacterium capable of producing the substance to produce the substance and collecting the substance,
   wherein the bacterium harbors a DNA construct comprising the expression control sequence of the present invention, a promoter linked upstream of the expression sequence and a target gene which has relationship to production of the target substance and is linked downstream of the expression control sequence, and an intracellular concentration of an amino acid (sense amino acid) on which expression control by the expression control sequence depend, is changed to control expression of the target gene.

Examples of the target substance include CAT, and other prokaryotic enzymes, foreign protein products, amino acids, nucleotides and nucleosides, vitamins, and other biological active substances.

Examples of the bacterium capable of producing the target substance include bacteria belonging to the genuses *Escherichia*, *Salmonella*, and *Serratia*.

The culture conditions are not restricted provided that the bacterium capable of producing the target substance can produce the target substance. The conditions are properly selected depending on the bacterium.

Cultivation is usually carried out under an aerobic condition for 10 to 50 hours. The cultivation temperature is usually controlled at 28 to 37° C., and pH is usually controlled at 6.6 to 7.4 during cultivation. Inorganic or organic, acidic or alkaline substances as well as ammonia gas or the like can be used for pH adjustment.

The medium may be an ordinary medium containing a carbon source, a nitrogen source, organic ions and optionally other organic components.

As the carbon source, it is possible to use sugars such as glucose, lactose, galactose, fructose, sucrose or starch hydrolysate; alcohols such as glycerol or sorbitol; or organic acids such as fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as vitamin $B_1$ or yeast extract to be contained in appropriate amounts as organic trace nutrients. Other than the above, potassium phosphate, magnesium sulfate, iron ion, manganese ion and the like are added in small amounts, if necessary.

Collection of the target substance from a culture such as cells and a culture medium can be usually carried out by combining an ion exchange resin method, a precipitation method and other known methods.

The DNA construct may be as described above with respect to the expression control sequence provided that a gene which has relationship to production of the target substance is used as the target gene. Examples of the target gene which has relationship to production of the target substance include biosynthesis genes for the target substance, genes for production of energy and related substances such as intermediates used for biosynthesis of the target substance, regulatory genes therefor and the like. Specific examples thereof include L-tryptophan biosynthetic genes, L-serine biosynthetic genes (for L-tryptophan biosynthesis, in particular), pntAB genes, genes of $H^+$-ATPase.

In particular, if L-tryptophan is used as the sense amino acid and an L-serine biosynthetic gene, as the target gene, is linked downstream from the expression control sequence of the present invention in an L-tryptophan-producing bacterium, the expression of the L-serine biosynthetic gene increases when an intracellular accumulation amount of L-tryptophan increases. The time when the intracellular accumulation of L-tryptophan increases corresponds to the time when L-serine, which is one of substrates for L-tryptophan biosynthesis, decreases. Therefore, the expression of the L-serine biosynthetic gene can be increased only when L-serine decreases. On the other hand, it is not always possible for the L-serine biosynthetic gene to be highly expressed in the L-tryptophan-producing bacterium, because a high concentration of L-serine is detrimental to growth of cells. Accordingly, it is appreciated that the expression control sequence of the present invention is very useful when it is intended to increase the expression of the L-serine biosynthetic gene in the L-tryptophan-producing bacterium.

The bacterium which is capable of producing the target substance and harbors the DNA construct may be obtained by allowing a bacterium capable of producing the target substance to harbor the DNA construct or conferring the ability to produce the target substance on a bacterium harboring the DNA construct. The allowing the bacterium to harbor the DNA construct can be carried out according to standard gene engineering techniques. Conferance of the ability to produce the target substance can be carried out according to the known method. For example, when the target substance is CAT, a method of introduction of a DNA encoding the chloramphenicol acetyl transferase can be used.

The method of changing an intracellular concentration of the sense amino acid, is exemplified by a method of changing a concentration of the sense amino acid in the medium in which the bacterium is cultured, a method of changing an amount of synthesis or degradation of the sense amino acid in cells. The method of changing an amount of synthesis or degradation of the sense amino acid in cells is preferable, because the production of the target substance can be couple with the production of an intermediate and the like for the target substance production. The change of the target gene expression can be determined by measuring an amount of the gene product of the target gene, or an activity of the gene product when the gene product has the activity.

EXAMPLES

Example 1

Construction of the Recombinant Plasmids Carrying the Native Attenuator and the Artificial Anti-attenuators and Their Fragments 1. Construction of the Vector Plasmid pML-$P_{tac}$-ter_thrL-cat The plasmid vector pML-$P_{tac}$-ter_thrL-cat carrying a ColE1-like replicon, $Ap^R$-gene as a selective marker, the tac promoter ($P_{tac}$)(Russel D. R., Bennett G., Gene 20 (1982) 231), synthetic ρ-independent transcription terminator of the leader peptide of the E. coli thr-operon (ter_thrL) and the structural region of cat-gene downstream of $P_{tac}$, has been constructed in the following manner. The gene cat transcribing from $P_{tac}$, has been used as a reporter in the experiments described below.

1.1. Construction of the pML-pp-vector

Figure 4:
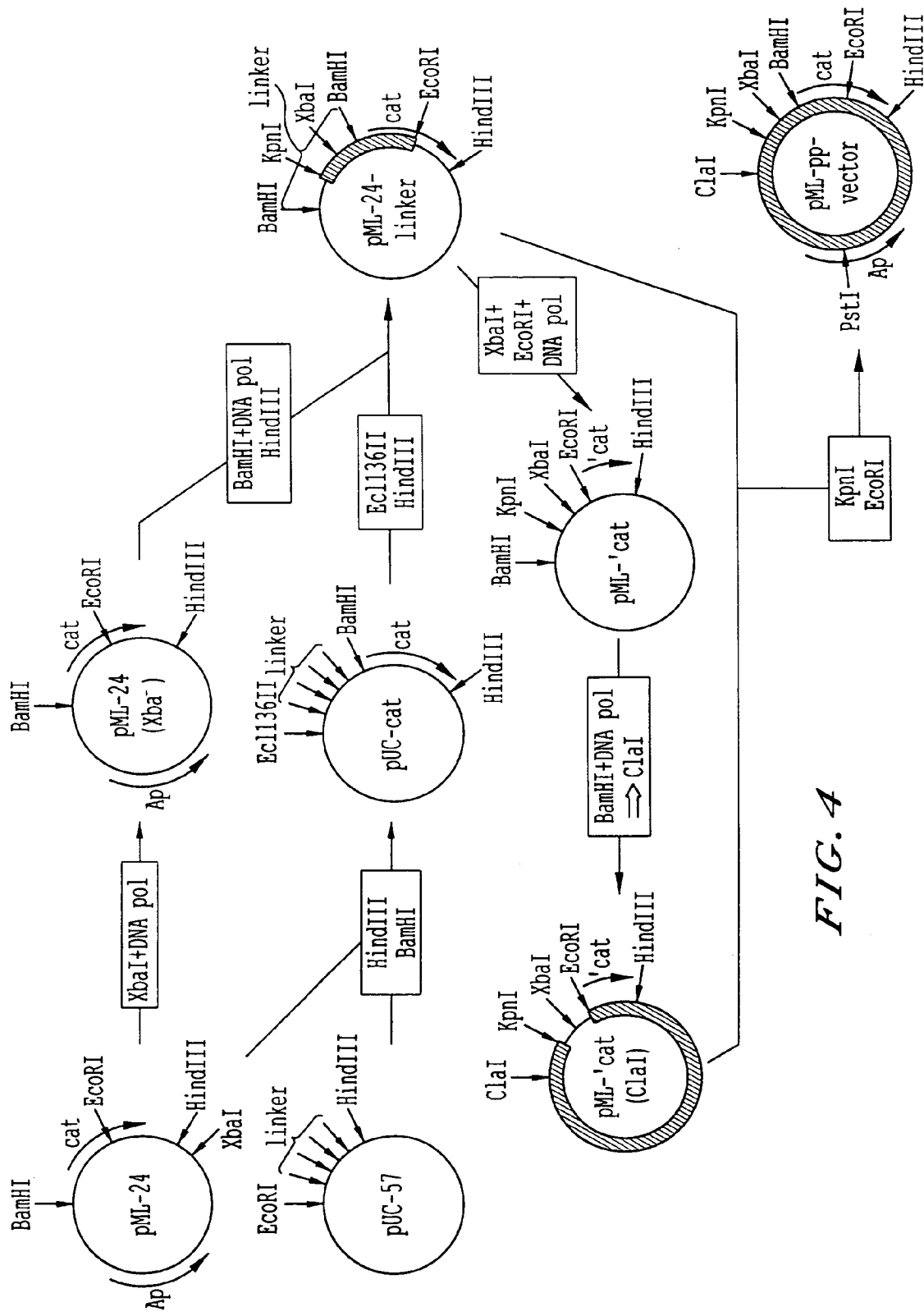
FIG. 4 shows the scheme of construction of the plasmid in Example 1.

Two plasmids were used as the progenitors for pML-pp-vector construction. The first plasmid was the present inventors' previously described plasmid pML24 (Trukhan et al., Biotechnologiya (in Russian) 4, No. 3 (1988) 325-334). The second plasmid was the commercially available (MBI "Fermentas", Lithuania) vector pUC57 (GenBank/EMBL accession number Y14837). The construction scheme of the pML-pp-vector was based on the standard gene engineering procedures (Sambrook et al., "Molecular cloning. Laboratory manual". (1989) Second Edition, Cold Spring Harbor Laboratory Press) presented in the FIG. 4.

1.2. Insertion of the Chemically Synthesized ter_thrL in the Plasmid pML-pp-vector The synthetic ρ-independent transcription terminator of the E. coli thr-operon leader peptide has been constructed by annealing two chemically synthesized oligonucleotides with the following sequences:

I—5'-ctagaaagcttaacacagaaaaaagcccgcacctgacagtgcgggcttt ttttttcgaccactgcagg→3' (SEQ ID NO: 4), and II—5'-gatccctgcagtggtcgaaaaaaaaagcccgcactgtcaggtgcgggc tttttctgtgttaagcttt→3' (SEQ ID NO: 5).

Subsequent to annealing, the resultant double-stranded DNA fragment has single-stranded "cohesive" ends corresponding to XbaI- and BamHI-derived DNA.

The fragment is phosphorylated by T4 polynucleotide kinase according to standard protocols and cloned in the plasmid pML-pp-vector, which has been cleaved by XbaI and BamHI. The correlation between the desired and obtained plasmid structure has been established due to restriction analysis and DNA sequencing of the inserted fragment.

1.3. Molecular Cloning of $P_{tac}$

PCR-driven DNA amplification has been provided for molecular cloning of the hybrid promoter ($P_{tac}$). Two oligonucleotide primers were chemically synthesized for this purpose:

(SEQ ID NO: 6)
III-5'-gcttaggtaccctccccatccccctgttgac→3',
and (SEQ ID NO: 7)
IV-5'-ctgtttctagatcctgtgtgaaattgttatccgc→3'.

The commercially available plasmid pDR540 (Pharmacia, Sweden) carrying $P_{tac}$-promoter, was used as a PCR template.

Figure 5:
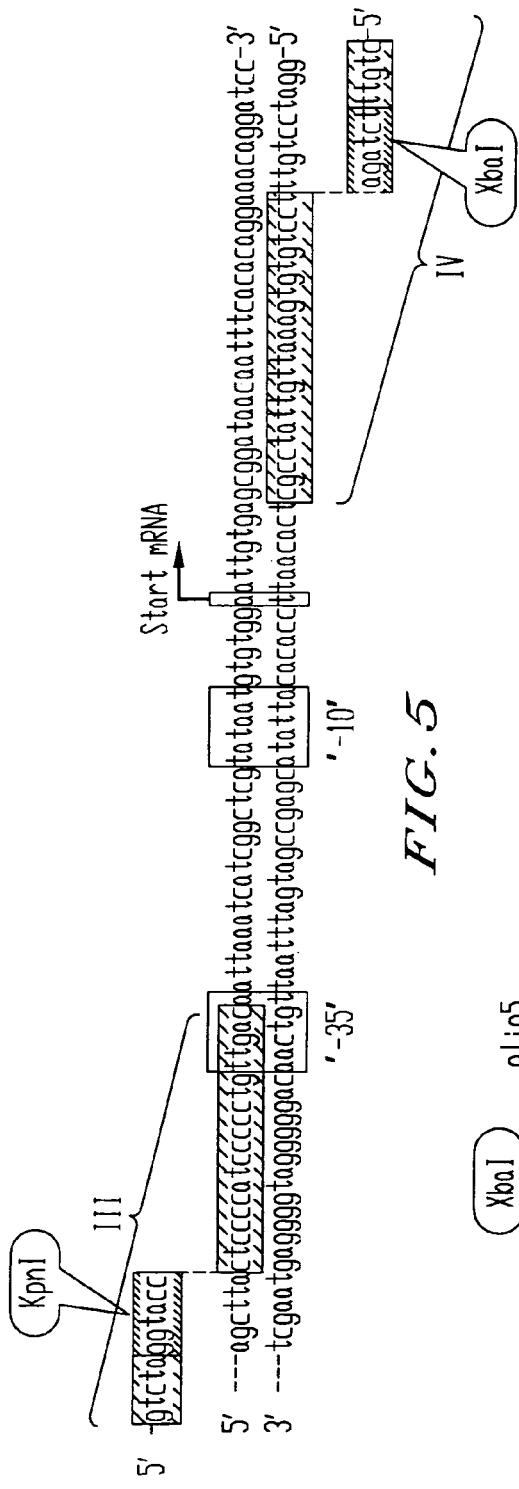
FIG. 5 shows the structure of the $P_{tac}$ promoter from the plasmid pDR540 (SEQ ID NO: 22 and its complementary 3'-5' sequence). The sequences of the "upstream" (III; SEQ ID NO: 6) and "downstream" (IV; SEQ ID NO: 7) primers for PCR are dot-meshed.

These oligonucleotides carried the sequences upstream (III) and downstream (IV) of the promoter as presented in the FIG. 5. Moreover, to facilitate molecular cloning, they carried the sequences recognized by several (KpnI and XbaI) restriction endonucleases (see, FIG. 5). The amplified DNA fragment was treated with KpnI and XbaI followed by ligation into the previously obtained (see, item 1.2) plasmid vector cleaved by the same restriction endonucleases. The selected recombinant plasmid was named as pML-$P_{tac}$→ter_thrL→cat and used as the vector in the following experiments.

2. Construction of the Plasmids with the Native and Artificial Transcription Regulatory Elements The pML-$P_{tac}$→ter_thrL→cat plasmid described above was used as a vector for creation of all plasmids of interest. Moreover, the following set of oligonucleotides was chemically synthesized:

```
olig1:
                                                 (SEQ ID NO: 8)
5'-cagagctctagaagttcacgtaaaaagggtatcgac-3';

olig2:
                                                 (SEQ ID NO: 9)
5'-gtatcgcatatgaaagcaattttcgtactgaaagg-3';

olig3:
                                                 (SEQ ID NO: 10)
5'-gtctgagatctagtatctgattgctttacgcatggtg-3';

olig4:
                                                 (SEQ ID NO: 11)
5'-atcataggatcctaattttgttcaaaaaaaagcccgctcatt-3';

olig5:
                                                 (SEQ ID NO: 12)
5'-cgactgtctagaacggtacagaaagccccggcagat-3';

cat3':
                                                 (SEQ ID NO: 13)
5'-agctcaccgtctttcattgccatacgg-3';

cr5':
                                                 (SEQ ID NO: 14)
5'-acatgcggtaccgatcccgcgaaattaatacg-3'.
```

These oligonucleotides were used as the primers for the PCR-driven DNA amplification, as described below. The other set of oligonucleotides:

```
olig6:
5'-cagagctctagaagatctgcccgactgcgta      (SEQ ID NO: 15)
caacggtacagaaag ccccggcagatcacctgc-
3';

olig7:
5'-cggggcttttttattgcgcggttgataacg       (SEQ ID NO: 16)
ggatccagcgta-3';

olig8:
5'-tacgctggatcccgttatcaaccgcgcaata      (SEQ ID NO: 17)
aaaaagcccccggca ggtgatctgccggggct
t-3';

olig9:
5'-tctgtaccgttgtacgcagtcgggcagatct     (SEQ ID NO: 18)
tctagagctctg-3',
``` was used directly for reconstruction of the 3'-terminal region of the new artificial anti-attenuator (see, below).

2.1. Construction of the Plasmid pML-P$_{tac}$-an3:an4(an4:an5)-cat

Figure 6:
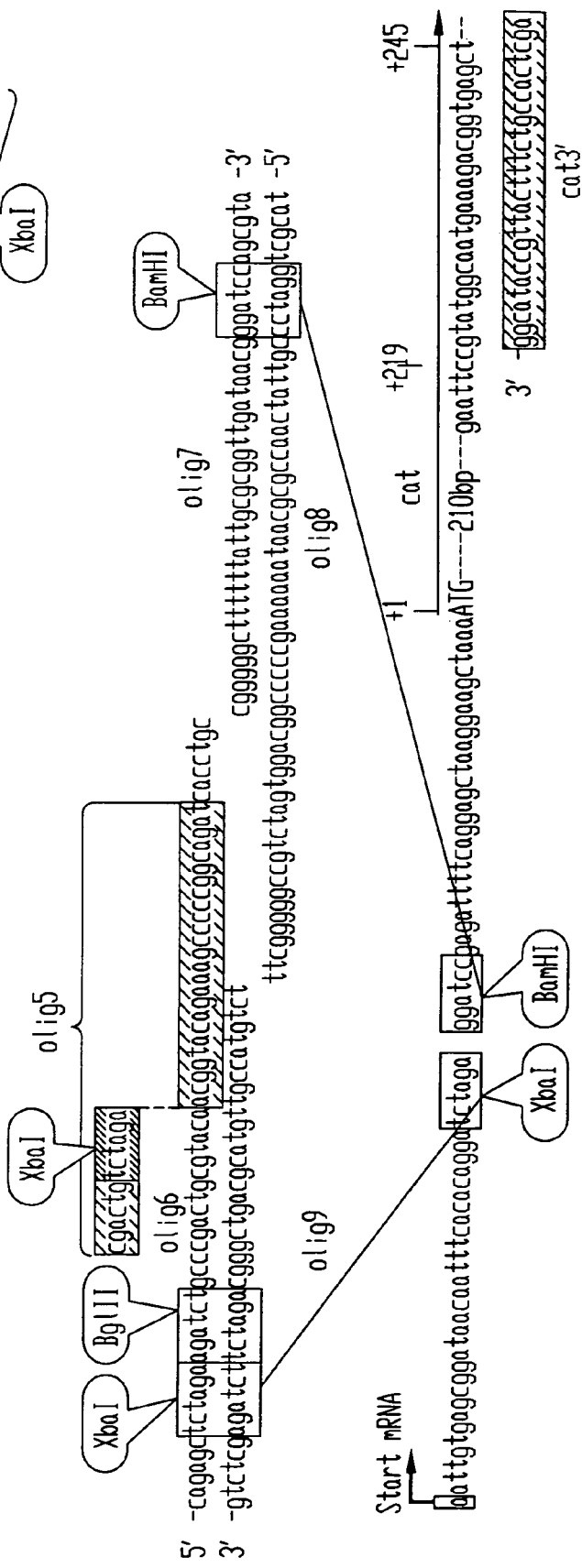
FIG. 6 shows the structure of chemically synthesized an3: an4 (an4:an5) fragment and the way the fragment was inserted into the cloning vector. Olig5 corresponds to SEQ ID NO: 12, olig6 corresponds to SEQ ID NO: 15, olig7 corresponds to SEQ ID NO: 16, olig8 corresponds to SEQ ID NO: 17, olig9 corresponds to SEQ ID NO: 18, cat3' corresponds to SEQ ID NO: 13, the sequence starting with "start mRNA" and ending with XbaI corresponds to SEQ ID NO: 23, and the sequence starting with BamHI and ending with "+245" corresponds to SEQ ID NO: 24.

This plasmid was constructed on the basis of pML-P$_{tac}$→ter_thrL→cat with the insertion of the double-stranded DNA fragment created from the chemically synthesized oligonucleotides (olig6, olig7, olig8 and olig9), instead of ter_thrL between promoter P$_{tac}$ and the structural region of cat-gene (see, FIG. 6). For this purpose initially 650 ng of olig7 and 650 ng of olig9 were phosphorylated using the T4 polynucleotidekinase ("MBI Fermentas", Lithuania) according to the recommended protocol. Two mixtures contained 430 ng of olig6 plus 650 ng of phosphorylated olig9 and 430 ng of olig8 plus 650 ng of phosphorylated olig7 in 30 μl of the "Y+/Tango" buffer ("MBI Fermentas", Lithuania) was heated at 100° C. for 5 min and then annealed at 75° C. for 5 min. Subsequently the mixtures were mixed together, heated at 60° C. for 5 min and annealed at 20° C. for 10 min. To the annealed DNA, 5 units of T4 DNA ligase ("MBI Fermentas", Lithuania) were added along with 0.5 μl of 100 mM ATP and incubation at 22° C. for 4 hours and overnight incubation at +4° C.

Following overnight incubation, the mixture was heated at 68° C. for 10 min and loaded on gel-electrophoresis. The well-seen DNA band was isolated using the Low-Melting-Point Agarose technique. The double-stranded DNA fragment (108 bp in length) obtained thereby was treated with XbaI ("MBI Fermentas", Lithuania) as recommended by producer. 360 ng of the digested fragment was ligated to 50 ng of vector pML-P$_{tac}$→ter_thrL→cat which was prepared from an E. coli (dam$^-$) strain and cleaved by XbaI.

In all cases, when the vector plasmid pML-P$_{tac}$→ter_thrL→cat and the recombinant plasmids obtained on its basis had to be cleaved using the restriction endonuclease XbaI, the plasmid DNA has to be provided from the E. coli (dam$^-$) strain because the XbaI-restriction site in these plasmids overlaps with the DAM recogntion sequence (GATC), and so the plasmid DNA purified from the E. coli (dam$^+$) strain could not be cleaved by XbaI due to methylation of the Dam site. Ligation was performed using 3 u of T4 DNA Ligase at +4° C. overnight. The obtained mixture was treated with BamHI ("MBI Fermentas", Lithuania) according to the standard protocol. Finally, the DNA mixture was diluted to 60 μl volume of T4 DNA Ligase buffer and was treated with 5 units of T4 DNA Ligase overnight at +4° C. The resulting mixture was transformed into the strain HB101 and colonies were screened for desired construction.

The plasmid pML-P$_{tac}$-an3:an4(an4:an5)-cat was obtained and its structure was confirmed by restriction analysis and DNA sequencing according to the standard Sanger's procedure. We suspect, that the obtained plasmid carries the DNA fragment which is transcribed, could provide the formation of anti-terminator hairpin an3:an4 (the terminator hairpin an4:an5 could not form because an3:an4 being synthesized earlier).

2.2. Construction of the Plasmid pML-P$_{tac}$-an4:an5-cat

The above described plasmid pML-P$_{tac}$-an3:an4(an4:an5)-cat was as a progenitor for construction the next recombinant DNA: it was as a template for PCR-driven DNA amplification of the fragment encoding the last, an4:an5, hairpin of the new regulatory region. In this PCR method, PCR the oligonucleotides: olig5 and cat3' were used as the primers (see, FIG. 6). The first of them corresponds to the beginning of those region of the earlier cloned fragment that encodes the hairpin an4:an5, but it also has the nucleotides recognized by XbaI near the 5'-terminus (see, FIG. 6). The second oligonucleotide, cat3', corresponds to the fragment of the coding region of the cat-gene (position +219-+245, if A from ATG-initiation codon of CAT is numbered as "+1") (see, FIG. 6). The double-stranded DNA fragment obtained by PCR, was treated by XbaI, ligated with the vector plasmid pML-P$_{tac}$→ter_thrL→cat cleaved by the same restriction endonuclease, followed by BamHI-treatment and recyclization of the product by T4 DNA ligase. So, the plasmid of interest, named pML-P$_{tac}$-an4:an5-cat, was obtained.

2.3. Construction of the Plasmid pML-P$_{tac}$-trpL-cat

Figures 7, 8:
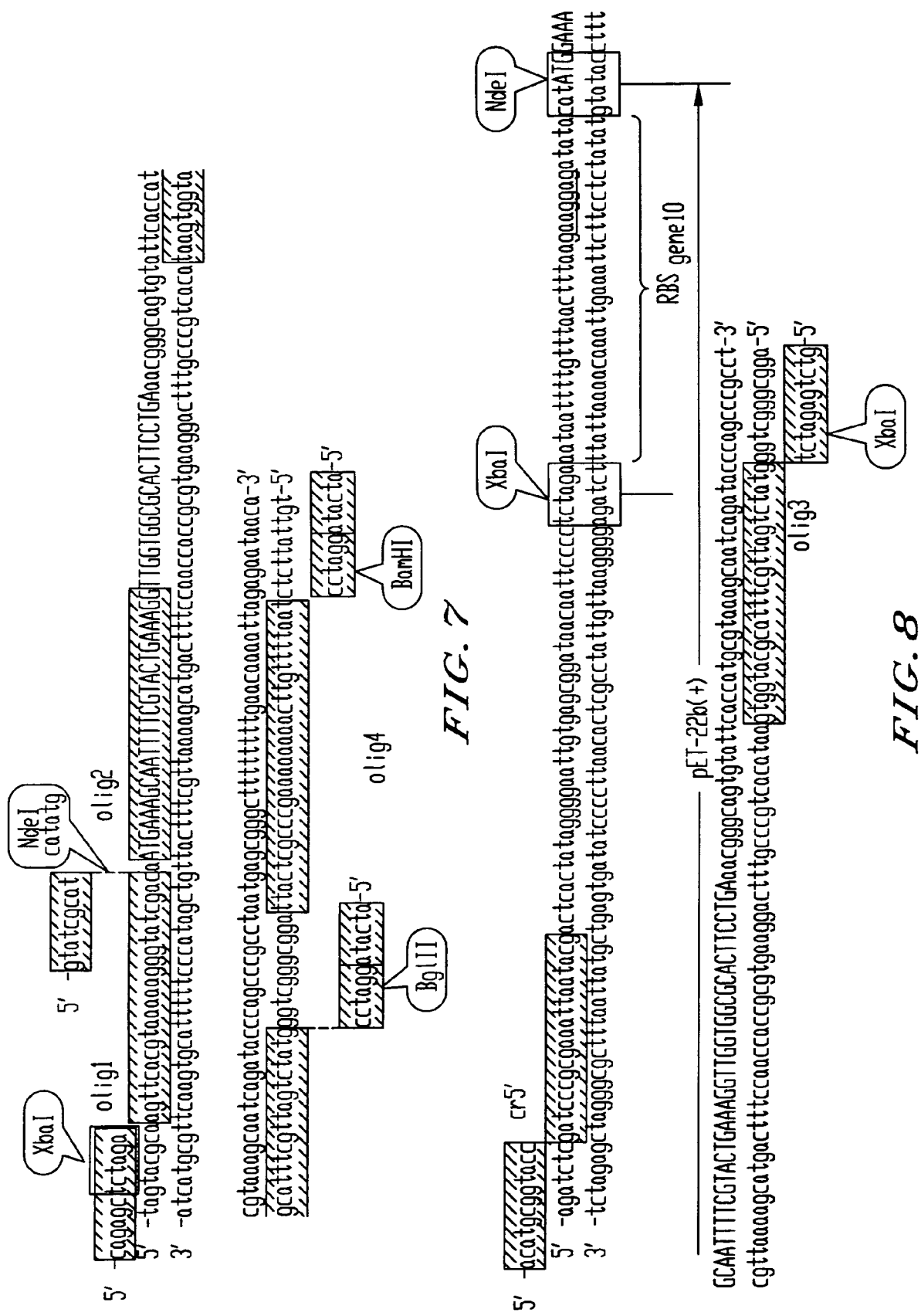
FIG. 7 shows the structure of the native attenuator region of the E. coli trp-operon. The leader peptide is shown in capital italic letters. Olig1 corresponds to SEQ ID NO: 8, olig2 corresponds to SEQ ID NO: 9, olig3 corresponds to SEQ ID NO: 10, olig4 corresponds to SEQ ID NO: 11, and the full-length 5'-3' sequence corresponds to SEQ ID NO: 25 (the complementary 3'-5' sequence is also presented).
FIG. 8 shows the structure of the intermediate construction including fusion between RBS of bacteriophage T7 gene10 and the leader region of trp operon. The leader peptide is shown in capital italic letters. Olig3 corresponds to SEQ ID NO: 10, cr5' corresponds to SEQ ID NO: 13, and the full-length 5'-3' sequence corresponds to SEQ ID NO: 26 (the complementary 3'-5' sequence is also presented).

For construction of plasmid carrying the native gene of the E. coli trp-operon leader peptide (gene trpL) under the transcriptional control of P$_{tac}$-promoter, chromosomal DNA from E. coli MG1655, the whole genome sequence of which had been determined, was used as a PCR template. The oligonucleotides olig1 and olig4 corresponding to 5'- and 3'-terminal regions of the trpL-gene (see, FIG. 7), were used as the primers for DNA amplification. As is shown in FIG. 7, these primers also carry a flanking XbaI and BamHI (in olig1 and olig4, respectively) recognition sites for the convenience of the following manipulation. The double-stranded DNA fragment, 175 bp in length, was treated with XbaI and BamHI followed by cloning in the plasmid vector pML-P$_{tac}$→ter_thrL→cat, which was cleaved using the same restriction endonucleases. The obtained plasmid carrying the native trpL-gene instead of ter_thrL in the vector plasmid, was named as pML-P$_{tac}$-trpL-cat.

2.4. Construction of the Plasmid pML-P$_{tac}$-anti_att-I-cat

The above described plasmid pML-P$_{tac}$-trpL-cat was used as a PCR template for creation of the next recombinant DNA. In this procedure the previously described oligonucleotide, olig1, as well as the olig3 was used as the primers. The olig3 corresponds to the central region of the native trpL-gene and also carries the BglII-recognition site at its 5'-terminus (see, FIG. 7). After PCR-driven DNA amplification the obtained double-stranded fragment 133 bp in length was treated with XbaI, ligated with the plasmid pML-P$_{tac}$-an3:an4(an4:an5)-cat cleaved by the same restriction endonuclease, followed by hydrolysis of the product with BglII and recyclization by T4 DNA ligase. The obtained plasmid carrying the artificial anti-attenuator between P$_{tac}$-promoter and the structural region of the cat-gene, was named as pML-P$_{tac}$-anti_att-I-cat.

2.5. Construction of the Plasmid pML-P$_{tac}$-anti_att-II-cat

The construction of the recombinant plasmid carrying the artificial anti-attenuator with the high-efficient ribosome binding site (RBS) of the phage T7 gene10 upstream the coding region of the native leader peptide of the E. coli trp-operon, was provided in the following manner. Initially, the double-stranded DNA fragment was obtained from PCR using olig2 (see, FIG. 7) and olig3 as the primers and DNA of the plasmid pML-P$_{tac}$-trpL-cat as a template. So, the restriction site for NdeI was reconstructed upstream of ATG-initiating codon of the leader peptide (the nucleotides of ATG-codon are the region of the sequence CATATG recognized by NdeI). The obtained DNA fragment cleaved by NdeI was ligated with the commercially available ("Novagen", USA) plasmid vector pET-22b(+) treated by NdeI. The plasmid pET-22b(+) carries RBS of T7 gene10 between XbaI and NdeI restriction sites.

The product of this ligation was used as a template for the PCR at the next stage of construction. The new oligonucleotide cr5' (see, FIG. 8), as well as the previously exploited olig3, were used as the primers for this PCR. The obtained double-stranded DNA fragment 210 bp in length, was treated by XbaI and BglII and cloned in the plasmid pML-P$_{tac}$-an3:an4(an4:an5)-cat according to the protocol exploited for construction of pML-P$_{tac}$-anti_att-I-cat. So, the new plasmid named as pML-P$_{tac}$-anti-att-II-cat carrying the artificial anti-attenuator with RBS of phage T7 gene10 in the 5'-untranslated region of the trp leader peptide gene, was produced. The structures of all plasmids carrying the artificial transcriptional regulatory elements, were confirmed by the restriction analysis and sequencing according to the standard Sanger's procedure.

Example 2

The Detection of the Accumulation Levels of Cat Protein in Strains Carrying the Recombinant Plasmids With the Native trpL, the Artificial Anti-attenuators and Their Fragments The previously described plasmids (see, Example 1): pML-P$_{tac}$-an4:an5-cat, pML-P$_{tac}$-an3:an4(an4:an5)-cat, pML-P$_{tac}$-trpL-cat, pML-P$_{tac}$-anti_att-I-cat, pML-P$_{tac}$-anti_att-II-cat were introduced into E. coli TG1 (supE, hsd, thi, Δ(lac-proAB), F'[traD36, proAB$^+$, lacI$^Q$, lacZΔM15]) and E. coli B7248 (trpB$^-$:Tn10, Str$^R$) according to the standard experimental protocols with the selection of the plasmid-carrier cells on the medium with the ampicillin (100 µg/ml) addition (Sambrook et al., "Molecular cloning. Laboratory manual". (1989) Second Edition, Cold Spring Harbor Laboratory Press). The obtained cell cultures were grown in the tubes with the liquid medium at 37° C. with good aeration. As for the cultivation medium, the L-broth with the ampicillin addition was used for the TG1-driven plasmid-carrier strains and the minimal M9-media with ampicillin (100 µg/ml), thiamine (5 µg/ml) and tryptophan (10 µg/ml) for the strains constructed on the basis of E. coli B7248. The overnight B7248-driven cultures were diluted in 50 times with the same cultural media and the cultivation had been continued for 2-4 hours until the optical density at 600 nm being 1 (OD$_{600}$=1). Each of the culture media was divided into two parts and tryptophan (200 µg/ml) was added to the one of two portions.

Cultivation was continued for 1 hour, followed by cell collection by centrifugation, washed with physiological solution and resuspended in 1/10 of the initial volume of potassium-phosphate buffer. Then cells were sonicated and debris was harvested by centrifugation at 4° C. The protein concentration in the supernatants was measured using the Bio-Rad Coumassie R250 reagent according to the protocols described by the producer. The chloramphenicol-acetyltransferase activity was measured according to the conventional method (Schottel J L, Sninsky J J, Cohen S N "Effects of alterations in the translation control region on bacterial gene expression: use of cat gene constructs transcribed from the lac promoter as a model system." Gene, 28 (1984) 177-193). In these experiments the 5,5'-dithio-bis(2-nitrobenzoic acid)— the Ellman's reagent ("Sigma") was used as a specific reagent. The results obtained are shown in Table 1 above.

SDS-PAGE (0.1% SDS—12.5% PAAG electrophoresis) was performed to visualize the accumulated CAT in the E. coli TG1-driven plasmid-carrier strains. Each strain was grown as described above and each culture was divided into two parts. The cultures were supplemented with IPTG (up to 0.4 mM of the final concentration) and cultured for 2 hours. The cells were harvested, resuspended in SDS-sample loading buffer (60 mM Tris-HCl pH6.8/2.3% SDS/10% glycerol/ 5% β-mercaptoethanol), and boiled for 15 minutes. 10-20 µl of the resulting suspension was loaded on PAAG and electrophoration was performed according to the method described by Laemmli (Laemmli V. K.//"Cleavage of structural proteins during the assembly of the head of bacteriophage T4". Nature 227 (1970) 680-685). The gel was stained by Coomassie-blue for detecting the separated proteins. The corresponding patterns of the gels obtained above are presented in the FIG. 3.

What is claimed is:

1. An expression control sequence which controls expression of a target gene linked downstream of the expression control sequence depending on an intracellular concentration of an amino acid, wherein in a bacterium which harbors a DNA construct comprising the expression control sequence, a promoter linked upstream of the expression control sequence and the target gene linked downstream of the expression control sequence, frequency of termination in the expression control sequence when transcription initiates from the promoter is decreased due to an increase in the intracellular concentration of an amino acid, whereby expression of the target gene increases, wherein said expression control sequence comprises a region coding for a leader peptide comprising said amino acid and a ρ independent terminator, wherein when translation of the leader peptide stops at codon of said amino acid in the course of the translation in case of starvation of said amino acid, a base paring structure of the ρ independent terminator is formed in a transcript of the expression control sequence, whereby the frequency of termination in the expression control sequence, of the transcription increases;

wherein said expression control sequence comprises five segments which are from an attenuator of a tryptophan operon of Escherichia coli and an attenuator of a histidine operon of Escherichia coli when the five segments are numbered in order from an upstream side, the first and second segments, and a coding region for the leader peptide comprise the corresponding part of the attenuator of the tryptophan operon, the fourth and fifth segments comprise the corresponding part of the attenuator of the histidine operon, and the third segment comprises a combination of the corresponding parts of the attenuators of the tryptophan operon and the histidine operon;

wherein the first segment overlaps with codon of the amino acid in the leader peptide; and wherein the sequence of each segment or a part thereof and the sequence of the adjacent segment or a part thereof constitute an inverted repeat sequence.

2. The expression control sequence according to claim 1, wherein the leader peptide has been modified to contain not less than 2 tryptophan residues.

3. A genetic construct comprising the expression control sequence according to claim 1, a promoter linked upstream of the expression control sequence, and a target gene linked downstream of the expression control sequence.

4. The genetic construct according to claim 3, wherein said target gene is chloramphenicolacetyltransferase gene (cat).

5. The genetic construct according to claim 3 wherein said target gene is an amino acid operon.

6. The genetic construct according to claim 3, wherein said target gene is a gene encoding an enzyme involved in amino acid biosynthesis, nucleoside biosynthesis, or nucleotide biosynthesis.

7. The genetic construct according to claim 3, wherein said promoter is a regulated prokaryotic promoter.

8. The genetic construct according to claim 3, wherein said promoter is a constitutive prokaryotic promoter.

9. The genetic construct according to claim 3, wherein said promoter is $P_{tac}$.

10. The expression control sequence of claim 1, which comprises the sequence of SEQ ID NO: 21 and wherein said amino acid is tryptophan.

11. A method for controlling expression of a target gene, comprising transforming a bacterium with a genetic construct comprising an expression control sequence, cultivating said bacterium in a culture medium, and changing an intracellular concentration of an amino acid on which expression control by the expression control sequence depend, to control expression of the target gene, wherein the expression control sequence is an expression control sequence which controls expression of a target gene linked downstream of the expression control sequence depending on an intracellular concentration of an amino acid, wherein in a bacterium which harbors a DNA construct comprising the expression control sequence, a promoter linked upstream of the expression control sequence and the target gene linked downstream of the expression control sequence, frequency of termination in the expression control sequence when transcription initiates from the promoter is decreased due to an increase in the intracellular concentration of an amino acid, whereby expression of the target gene increases, wherein said expression control sequence comprises a region coding for a leader peptide comprising said amino acid and a ρ independent terminator, wherein when translation of the leader peptide stops at codon of said amino acid in the course of the translation in case of starvation of said amino acid, a base pairing structure of the ρ independent terminator is formed in a transcript of the expression control sequence, whereby the frequency of termination in the expression control sequence, of the transcription increases;

wherein said expression control sequence comprises five segments which are from an attenuator of a tryptophan operon of *Escherichia coli* and an attenuator of a histidine operon of *Escherichia coli* when the five segments are numbered in order from an upstream side, the first and second segments, and a coding region for the leader peptide comprise the corresponding part of the attenuator of the tryptophan operon, the fourth and fifth segments comprise the corresponding part of the attenuator of the histidine operon, and the third segment comprises a combination of the corresponding parts of the attenuators of the tryptophan operon and the histidine operon;

wherein the first segment overlaps with codon of the amino acid in the leader peptide; and wherein the sequence of each segment or a part thereof and the sequence of the adjacent segment or a part thereof constitute an inverted repeat sequence.

12. The method according to claim 11, wherein said bacterium belongs to the genus *Escherichia*, the genus *Salmonella*, or the genus *Serratia*.

13. The method according to claim 12, wherein said bacterium belongs to the genus *Escherichia*.

14. The method according to claim 11, wherein said amino acid is tryptophan.

15. The method according to claim 14, which expression control sequence comprises the sequence of SEQ ID NO: 21.

16. A method for producing a target substance comprising cultivating a bacterium comprising a genetic construct in a culture medium, changing an intracellular concentration of an amino acid on which expression control by the expression control sequence depend, to control expression of the target gene, and collecting the target substance, wherein the genetic construct comprises an expression control sequence, a promoter linked upstream of the expression control sequence, and a target gene linked downstream of the expression control sequence;

wherein the expression control sequence is an expression control sequence which controls expression of a target gene linked downstream of the expression control sequence depending on an intracellular concentration of an amino acid, wherein in a bacterium which harbors a DNA construct comprising the expression control sequence, a promoter linked upstream of the expression control sequence and the target gene linked downstream of the expression control sequence, frequency of termination in the expression control sequence when transcription initiates from the promoter is decreased due to an increase in the intracellular concentration of an amino acid, whereby expression of the target gene increases, wherein said expression control sequence comprises a region coding for a leader peptide comprising said amino acid and a ρ independent terminator, wherein when translation of the leader peptide stops at codon of said amino acid in the course of the translation in case of starvation of said amino acid, a base pairing structure of the ρ independent terminator is formed in a transcript of the expression control sequence, whereby the frequency of termination in the expression control sequence, of the transcription increases;

wherein said expression control sequence comprises five segments which are from an attenuator of a tryptophan operon of *Escherichia coli* and an attenuator of a histidine operon of *Escherichia coli* when the five segments are numbered in order from an upstream side, the first and second segments, and a coding region for the leader peptide comprise the corresponding part of the attenuator of the tryptophan operon, the fourth and fifth segments comprise the corresponding part of the attenuator of the histidine operon, and the third segment comprises a combination of the corresponding parts of the attenuators of the tryptophan operon and the histidine operon;

wherein the first segment overlaps with codon of the amino acid in the leader peptide; and wherein the sequence of each segment or a part thereof and the sequence of the adjacent segment or a part thereof constitute an inverted repeat sequence.

17. The method according to claim 16, wherein the intracellular concentration of the amino acid is changed by synthesis or degradation of the amino acid by the bacterium.

18. The method according to claim 16, wherein said bacterium belongs to the genus *Escherichia*, the genus *Salmonella*, or the genus *Serratia*.

19. The method according to claim 18, wherein said bacterium belongs to the genus *Escherichia*.

20. The method according to claim 16, wherein said amino acid is tryptophan.

21. The method according to claim 20, which expression control sequence comprises the sequence of SEQ ID NO: 21.

* * * * *

SEQUENCE LISTING

```
<160> NUMBER OF SEQ ID NOS: 26

<210> SEQ ID NO 1
<211> LENGTH: 118
<212> TYPE: DNA
<213> ORGANISM: Escherichia coli
```

<400> SEQUENCE: 1

```
atgaaagcaa ttttcgtact gaaaggttgg tggcgcactt cctgaaacgg gcagtgtatt    60
caccatgcgt aaagcaatca gatacccagc ccgcctaatg agcgggcttt tttttgaa     118
```

<210> SEQ ID NO 2
<211> LENGTH: 153
<212> TYPE: DNA
<213> ORGANISM: Escherichia coli

<400> SEQUENCE: 2

```
atgacacgcg ttcaatttaa acaccaccat catcaccatc atcctgacta gtctttcagg    60
cgatgtgtgc tggaagacat tcagatcttc cagtggtgca tgaacgcatg agaaagcccc   120
cggaagatca ccttccgggg ctttttttat tgc                                153
```

<210> SEQ ID NO 3
<211> LENGTH: 169
<212> TYPE: DNA
<213> ORGANISM: Artificial sequence
<220> FEATURE:
<223> OTHER INFORMATION: Synthetic DNA

<400> SEQUENCE: 3

```
atgaaagcaa ttttcgtact gaaaggttgg tggcgcactt cctgaaacgg gcagtgtatt    60
caccatgcgt aaagcaatca gatactagat ctgcccgact gcgtacaacg gtacagaaag   120
cccccggcag atcacctgcc ggggcttttt tattggcgg ttgataacg                169
```

<210> SEQ ID NO 4
<211> LENGTH: 69
<212> TYPE: DNA
<213> ORGANISM: Escherichia coli

<400> SEQUENCE: 4

```
ctagaaagct taacacagaa aaaagcccgc acctgacagt gcgggctttt tttttcgacc    60
actgcagga                                                           69
```

<210> SEQ ID NO 5
<211> LENGTH: 69
<212> TYPE: DNA
<213> ORGANISM: Escherichia coli

<400> SEQUENCE: 5

```
gatccctgca gtggtcgaaa aaaaagccc gcactgtcag gtgcgggctt ttttctgtgt    60
taagcttta                                                           69
```

<210> SEQ ID NO 6
<211> LENGTH: 32
<212> TYPE: DNA
<213> ORGANISM: Artificial sequence
<220> FEATURE:
<223> OTHER INFORMATION: Synthetic DNA

<400> SEQUENCE: 6

```
gcttaggtac cctccccatc ccctgttga ca                                  32
```

<210> SEQ ID NO 7
<211> LENGTH: 35
<212> TYPE: DNA
<213> ORGANISM: Artificial sequence
<220> FEATURE:
<223> OTHER INFORMATION: Synthetic DNA
```

-continued

<400> SEQUENCE: 7
ctgtttctag atcctgtgtg aaattgttat ccgca                                    35

<210> SEQ ID NO 8
<211> LENGTH: 36
<212> TYPE: DNA
<213> ORGANISM: Artificial sequence
<220> FEATURE:
<223> OTHER INFORMATION: Synthetic DNA

<400> SEQUENCE: 8
cagagctcta gaagttcacg taaaagggt atcgac                                    36

<210> SEQ ID NO 9
<211> LENGTH: 35
<212> TYPE: DNA
<213> ORGANISM: Artificial sequence
<220> FEATURE:
<223> OTHER INFORMATION: Synthetic DNA

<400> SEQUENCE: 9
gtatcgcata tgaaagcaat tttcgtactg aaagg                                    35

<210> SEQ ID NO 10
<211> LENGTH: 37
<212> TYPE: DNA
<213> ORGANISM: Artificial sequence
<220> FEATURE:
<223> OTHER INFORMATION: Synthetic DNA

<400> SEQUENCE: 10
gtctgagatc tagtatctga ttgctttacg catggtg                                  37

<210> SEQ ID NO 11
<211> LENGTH: 42
<212> TYPE: DNA
<213> ORGANISM: Artificial sequence
<220> FEATURE:
<223> OTHER INFORMATION: Synthetic DNA

<400> SEQUENCE: 11
atcataggat cctaattttg ttcaaaaaaa agcccgctca tt                            42

<210> SEQ ID NO 12
<211> LENGTH: 28
<212> TYPE: DNA
<213> ORGANISM: Artificial sequence
<220> FEATURE:
<223> OTHER INFORMATION: Synthetic DNA

<400> SEQUENCE: 12
agaacggtac agaaagcccc cggcagat                                            28

<210> SEQ ID NO 13
<211> LENGTH: 27
<212> TYPE: DNA
<213> ORGANISM: Artificial sequence
<220> FEATURE:
<223> OTHER INFORMATION: Synthetic DNA

<400> SEQUENCE: 13
agctcaccgt ctttcattgc catacgg                                             27

<210> SEQ ID NO 14
<211> LENGTH: 32

-continued

```
<212> TYPE: DNA
<213> ORGANISM: Artificial sequence
<220> FEATURE:
<223> OTHER INFORMATION: Synthetic DNA

<400> SEQUENCE: 14
acatgcggta ccgatcccgc gaaattaata cg                            32

<210> SEQ ID NO 15
<211> LENGTH: 65
<212> TYPE: DNA
<213> ORGANISM: Artificial sequence
<220> FEATURE:
<223> OTHER INFORMATION: Synthetic DNA

<400> SEQUENCE: 15
cagagctcta aagatctgc ccgactgcgt acaacggtac agaaagcccc cggcagatca    60
cctgc                                                              65

<210> SEQ ID NO 16
<211> LENGTH: 43
<212> TYPE: DNA
<213> ORGANISM: Artificial sequence
<220> FEATURE:
<223> OTHER INFORMATION: Synthetic DNA

<400> SEQUENCE: 16
cgggggcttt tttattgcgc ggttgataac gggatccagc gta                    43

<210> SEQ ID NO 17
<211> LENGTH: 65
<212> TYPE: DNA
<213> ORGANISM: Artificial sequence
<220> FEATURE:
<223> OTHER INFORMATION: Synthetic DNA

<400> SEQUENCE: 17
tacgctggat cccgttatca accgcgcaat aaaaaagccc ccggcaggtg atctgccggg    60
ggctt                                                              65

<210> SEQ ID NO 18
<211> LENGTH: 43
<212> TYPE: DNA
<213> ORGANISM: Artificial sequence
<220> FEATURE:
<223> OTHER INFORMATION: Synthetic DNA

<400> SEQUENCE: 18
tctgtaccgt tgtacgcagt cgggcagatc ttctagagct ctg                    43

<210> SEQ ID NO 19
<211> LENGTH: 118
<212> TYPE: DNA
<213> ORGANISM: Escherichia coli

<400> SEQUENCE: 19
atgaaagcaa ttttcgtact gaaaggttgg tggcgcactt cctgaaacgg gcagtgtatt    60
caccatgcgt aaagcaatca gatacccagc ccgcctaatg agcgggcttt tttttgaa    118

<210> SEQ ID NO 20
<211> LENGTH: 153
<212> TYPE: DNA
<213> ORGANISM: Escherichia coli

<400> SEQUENCE: 20
```

| | |
|---|---|
| atgacacgcg ttcaatttaa acaccaccat catcaccatc atcctgacta gtctttcagg | 60 |
| cgatgtgtgc tggaagacat tcagatcttc cagtggtgca tgaacgcatg agaaagcccc | 120 |
| cggaagatca ccttccgggg gcttttttat tgc | 153 |

<210> SEQ ID NO 21
<211> LENGTH: 169
<212> TYPE: DNA
<213> ORGANISM: Artificial sequence
<220> FEATURE:
<223> OTHER INFORMATION: Synthetic DNA

<400> SEQUENCE: 21

| | |
|---|---|
| atgaaagcaa ttttcgtact gaaaggttgg tggcgcactt cctgaaacgg gcagtgtatt | 60 |
| caccatgcgt aaagcaatca gatactagat ctgcccgact gcgtacaacg gtacagaaag | 120 |
| cccccggcag atcacctgcc gggggctttt ttattggcgg ttgataacg | 169 |

<210> SEQ ID NO 22
<211> LENGTH: 97
<212> TYPE: DNA
<213> ORGANISM: Artificial sequence
<220> FEATURE:
<223> OTHER INFORMATION: Synthetic DNA

<400> SEQUENCE: 22

| | |
|---|---|
| agcttactcc ccatcccct gttgacaatt aaatcatcgg ctcgtataat gtgtggaatt | 60 |
| gtgagcggat aacaatttca cacaggaaac aggatcc | 97 |

<210> SEQ ID NO 23
<211> LENGTH: 37
<212> TYPE: DNA
<213> ORGANISM: Artificial sequence
<220> FEATURE:
<223> OTHER INFORMATION: Synthetic DNA

<400> SEQUENCE: 23

| | |
|---|---|
| aattgtgagc ggataacaat ttcacacagg atctaga | 37 |

<210> SEQ ID NO 24
<211> LENGTH: 279
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (38)..(247)
<223> OTHER INFORMATION: n = a, c, g, or t

<400> SEQUENCE: 24

| | |
|---|---|
| ggatccgaga ttttcaggag ctaaggaagc taaaatgnnn nnnnnnnnn nnnnnnnnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnngaa ttccgtatgg caatgaaaga cggtgagct | 279 |

<210> SEQ ID NO 25
<211> LENGTH: 170
<212> TYPE: DNA
<213> ORGANISM: Artificial sequence
<220> FEATURE:
<223> OTHER INFORMATION: Synthetic DNA

```
<400> SEQUENCE: 25
tagtacgcaa gttcacgtaa aaagggtatc gacaatgaaa gcaattttcg tactgaaagg         60
ttggtggcgc acttcctgaa acgggcagtg tattcaccat gcgtaaagca atcagatacc        120
cagcccgcct aatgagcggg ctttttttg aacaaaatta gagaataaca                   170

<210> SEQ ID NO 26
<211> LENGTH: 205
<212> TYPE: DNA
<213> ORGANISM: Artificial sequence
<220> FEATURE:
<223> OTHER INFORMATION: Synthetic DNA

<400> SEQUENCE: 26
agatctcgat cccgcgaaat taatacgact cactataggg gaattgtgag cggataacaa         60
ttcccctcta gaaataattt tgtttaactt taagaaggag atatacatat ggaaagcaat        120
tttcgtactg aaaggttggt ggcgcacttc ctgaaacggg cagtgtattc accatgcgta        180
aagcaatcag atacccagcc cgcct                                             205
```